US012694992B1

(12) United States Patent　　(10) Patent No.: US 12,694,992 B1
Mortensen et al.　　(45) Date of Patent: Jul. 28, 2026

(54) SYSTEMS AND METHODS FOR ELECTRONICALLY COLLECTING AND LINKING STANDARDIZED CASE DATA IN A DATA WAREHOUSE

(71) Applicant: Veeva Systems Inc., Pleasanton, CA (US)

(72) Inventors: Marius K. Mortensen, Burlington (CA); Zhen Tan, North York (CA); Eric Mitchell Woolven, Toronto (CA); Sandra Komadinic, Hamilton (CA); Shanul Srivastava, Brampton (CA)

(73) Assignee: Veeva Systems Inc., Pleasanton, CA (US)

( * ) Notice: Subject to any disclaimer, the term of this patent is extended or adjusted under 35 U.S.C. 154(b) by 0 days.

(21) Appl. No.: 18/429,648

(22) Filed: Feb. 1, 2024

Related U.S. Application Data

(63) Continuation of application No. 17/871,516, filed on Jul. 22, 2022.

(51) Int. Cl.
　G16H 50/70　　(2018.01)
　G06F 16/215　　(2019.01)
(52) U.S. Cl.
　CPC ........... G16H 50/70 (2018.01); G06F 16/215 (2019.01)
(58) Field of Classification Search
　CPC .............................. G16H 50/70; G06F 16/215
　See application file for complete search history.

(56) References Cited

U.S. PATENT DOCUMENTS

| | | | |
|---|---|---|---|
| 9,147,047 B1 | 9/2015 | Grun et al. | |
| 9,239,722 B1 | 1/2016 | Calahan et al. | |
| 9,619,624 B2 | 4/2017 | Jackson et al. | |
| 9,626,479 B2 | 4/2017 | Zaleski | |
| 10,901,962 B2 | 1/2021 | Gubau i Forné et al. | |
| 10,942,936 B1 * | 3/2021 | Tan ..................... G06F 16/2445 | |
| 2002/0165853 A1 | 11/2002 | Gogolak | |
| 2006/0059137 A1 | 3/2006 | Walker | |
| 2006/0111847 A1 * | 5/2006 | Pearson ................. G16H 70/60 | |
| | | | 702/19 |

(Continued)

OTHER PUBLICATIONS

Harpaz, R., DuMouchel, W., LePendu, P., Bauer-Mehren, A., Ryan, P. and Shah, N.H. (2013), Performance of Pharmacovigilance Signal-Detection Algorithms for the FDA Adverse Event Reporting System. Clinical Pharmacology & Therapeutics, 93: 539-546. (Year: 2013).*

(Continued)

*Primary Examiner* — Matthew L Hamilton

(57)　　　　　ABSTRACT

A method for determining a potential signal includes receiving a request for case data and a statistical value minimum. The method further includes selecting the case data from the central case warehouse based on the request and determining a statistical value based on the case data. The statistical value is at least one of: a case count, a proportional reporting ratio (PRR) value, a chi-squared value, an Empirical Bayes (EB) value, or an Interaction Singal Score (INTSS) value. The method further includes determining the potential signal associated with a specific adverse event code and a medical product identifier based on the statistical value and the statistical value minimum. The method further includes outputting the statistical value and the potential signal via the secure network.

12 Claims, 11 Drawing Sheets

LIST OF DETECTED SIGNALS　　540

1-10 OF 10

| SIGNAL 548 | TRACKING | STATE | SOURCE | CASE COUNT (N) ▼ | PRR | χ² | EB05 | EBGM | EB95 |
|---|---|---|---|---|---|---|---|---|---|
| PI GASTRIC DISORDER 552 | ⊙ TRACK 554 556 | ○ NEW | FAERS 558 | 7221 560 | 20.15 562 | 125452.27 564 | 18.9 566 | 19.27 568 | 19.64 570 |
| PI GASTROINTESTINAL DISORDER | ⊙ TRACK | ○ NEW | FAERS | 3206 | 4.45 | 8490.13 | 4.28 | 4.41 | 4.54 |
| PI FOOD POISONING 552 | ⊙ TRACK 554 556 | ○ NEW | FAERS 558 | 147 560 | 3.22 562 | 223.25 564 | 2.75 566 | 3.15 568 | 3.6 570 |
| PI FUNCTIONAL GASTROINTESTINAL DISORDER | ⊙ TRACK | ○ NEW | FAERS | 117 | 1.83 | 52.49 | 1.64 | 1.91 | 2.22 |
| PI NEUROGENIC BOWEL 552 | ⊙ TRACK 554 556 | ○ NEW | FAERS 558 | 24 560 | 4.92 562 | 74.15 564 | 2.99 566 | 4.22 568 | 5.83 570 |
| PI STOMACH MASS | ⊙ TRACK | ○ NEW | FAERS | 11 | 1.43 | 1.43 | 0.8 | 1.33 | 2.11 |
| PI INTESTINAL MASS 552 | ⊙ TRACK | ○ NEW | FAERS | 10 | 0.7 | 1.25 | 0.4 | 0.59 | 1.11 |

548　554　556　　558　　560　562　　564　　566　　568　　570

500

(56) References Cited

U.S. PATENT DOCUMENTS

| | | | | |
|---|---|---|---|---|
| 2008/0300902 | A1* | 12/2008 | Smith | G16H 20/10 |
| | | | | 705/1.1 |
| 2009/0055378 | A1 | 2/2009 | Alecu et al. | |
| 2009/0158211 | A1* | 6/2009 | Gogolak | G16H 50/70 |
| | | | | 715/811 |
| 2009/0216555 | A1 | 8/2009 | Mitchell et al. | |
| 2009/0319299 | A1 | 12/2009 | De Vries et al. | |
| 2012/0036170 | A1 | 2/2012 | Triebel et al. | |
| 2012/0143776 | A1* | 6/2012 | Jaffe | G16H 50/50 |
| | | | | 705/317 |
| 2013/0179187 | A1* | 7/2013 | Jackson | G16H 20/10 |
| | | | | 705/3 |
| 2013/0225607 | A1* | 8/2013 | Gillies | A61P 7/02 |
| | | | | 514/274 |
| 2014/0122523 | A1 | 5/2014 | Aggarwal et al. | |
| 2014/0358576 | A1 | 12/2014 | Hoffman et al. | |
| 2015/0032679 | A1* | 1/2015 | Joseph | G16H 50/20 |
| | | | | 706/47 |
| 2016/0378950 | A1 | 12/2016 | Reiner | |
| 2018/0004902 | A1* | 1/2018 | Aronow | G16H 10/60 |
| 2018/0239991 | A1 | 8/2018 | Weller et al. | |
| 2018/0330300 | A1 | 11/2018 | Runkana et al. | |
| 2020/0294681 | A1 | 9/2020 | Routray et al. | |
| 2021/0315859 | A1* | 10/2021 | Bowen | A61P 25/18 |
| 2023/0048663 | A1 | 2/2023 | Doppalapudi et al. | |

OTHER PUBLICATIONS

Oracle Health Emperica Signal Sector Map, Internet Citation, 2 pages, URL: https://docs.oracle.com/health-sciences/empirica-signal-90/ESIUG/Home_page.htm#About_Signal_Configurations.htm, 2019.

Oracle Health Sciences Empirica Signal and Topics User Guide, Release 8.1, E70269-01, 2016.

Oracle® Health Sciences Empirica Signal 8.1, Signal Secure Configuration Guide, 2016, 27 pages.

Postigo, R., Brosch, S., Slattery, J et al. EudraVigilance Medicines Safety Database: Publicly Accessible Data for Research and Public Health Protection. Drug Saf 41, 665-675 (2018). (Year: 2018).

Curtis JR, Cheng H, Delzell E, Fram D, Kilgore M, Saag K, Yun H, Dumouchel W. Adaptation of Bayesian data mining algorithms to longitudinal claims data: coxib safety as an example. Med Care. Sep. 2008;46(9):969-75. doi: 10.1097/MLR.0b013e318179253b. PMID: 18725852; PMCID: PMC2694945. (Year: 2008).

* cited by examiner

200

```
┌─────────────────────────────────────────┐
│ RECEIVE HEALTH AGENCY CASE DATA FROM A   │ ⌐204
│ HEALTH AGENCY COMPUTING SYSTEM           │
└─────────────────────────────────────────┘
                    │
                    ▼
┌─────────────────────────────────────────┐
│ CLEAN THE HEALTH AGENCY CASE DATA        │ ⌐208
└─────────────────────────────────────────┘
                    │
                    ▼
┌─────────────────────────────────────────┐
│ RECEIVE MEDICAL PRODUCT DATA ASSOCIATED  │ ⌐210
│ WITH ONE OR MORE MEDICAL PRODUCTS        │
└─────────────────────────────────────────┘
                    │
                    ▼
┌─────────────────────────────────────────┐
│ RECEIVE A PLURALITY OF ADVERSE EVENT     │ ⌐211
│ IDENTIFIERS                              │
└─────────────────────────────────────────┘
                    │
                    ▼
┌─────────────────────────────────────────┐
│ COMBINE THE CLEANED HEALTH AGENCY CASE   │ ⌐212
│ DATA WITH THE MEDICAL PRODUCT DATA AND ONE│
│ OR MORE OF THE ADVERSE EVENT IDENTIFIERS │
└─────────────────────────────────────────┘
                    │
                    ▼
┌─────────────────────────────────────────┐
│ RECEIVE TRUSTED CASE DATA FROM A TRUSTED │ ⌐216
│ CASE REPOSITORY                          │
└─────────────────────────────────────────┘
                    │
                    ▼
┌─────────────────────────────────────────┐
│ MATCH THE COMBINED HEALTH AGENCY CASE    │ ⌐220
│ DATA WITH THE TRUSTED CASE DATA          │
└─────────────────────────────────────────┘
                    │
                    ▼
┌─────────────────────────────────────────┐
│ STORE THE TRUSTED CASE DATA AND          │ ⌐224
│ COMBINED HEALTH AGENCY CASE              │
│ DATA WITHIN A CENTRAL CASE DATA WAREHOUSE│
└─────────────────────────────────────────┘
                    │
                    ▼
┌─────────────────────────────────────────┐
│ RECEIVE A REQUEST FOR THE CASE DATA, THE │ ⌐228
│ REQUEST IDENTIFYING ONE OR MORE ELECTRONIC│
│ DATA SOURCES                             │
└─────────────────────────────────────────┘
```

SOURCE = HEALTH AGENCY CASE REPOSITORY

SOURCE = TRUSTED CASE REPOSITORY

SOURCE = TRUSTED CASE REPOSITORY AND HEALTH AGENCY CASE REPOSITORY

┌─────────────────────────────┐
│ OUTPUT THE COMBINED HEALTH   │ ⌐232
│ AGENCY CASE DATA             │
└─────────────────────────────┘

┌─────────────────────────────┐
│ OUTPUT THE TRUSTED CASE      │ ⌐236
│ DATA                         │
└─────────────────────────────┘

┌─────────────────────────────┐
│ OUTPUT THE TRUSTED CASE      │ ⌐240
│ DATA AND A PORTION OF        │
│ THE COMBINED HEALTH          │
│ AGENCY CASE DATA             │
└─────────────────────────────┘

FIG. 2

Figure 7A:
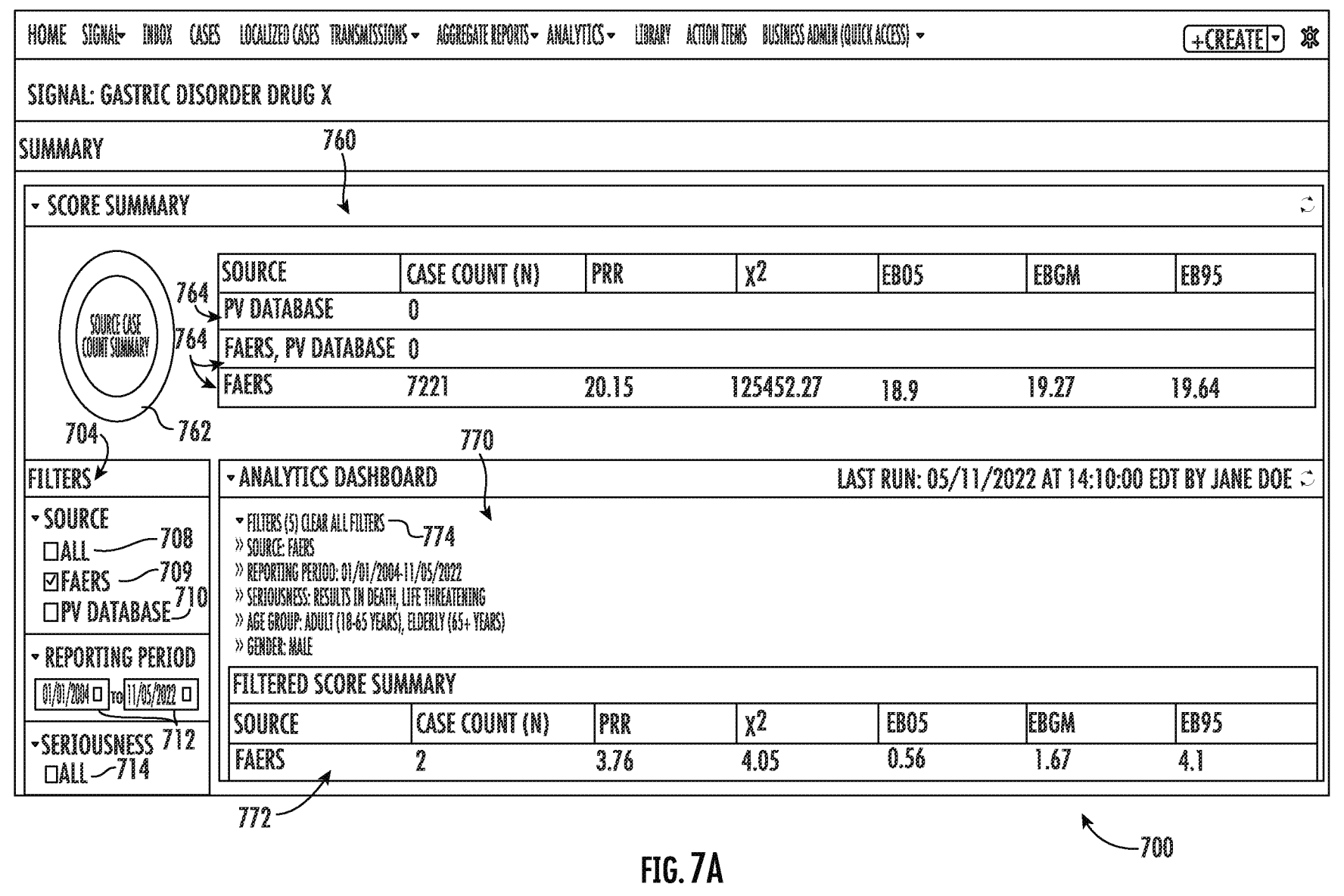

HOME   SIGNAL▶   INBOX   CASES   LOCALIZED CASES   TRANSMISSIONS▶   AGGREGATE REPORTS▶   ANALYTICS▶   LIBRARY   ACTION ITEMS   BUSINESS ADMIN (QUICK ACCESS)▶     [+CREATE]▶   ✿

SIGNAL: GASTRIC DISORDER DRUG X

SUMMARY   760

▶ SCORE SUMMARY

| SOURCE | CASE COUNT (N) | PRR | X2 | EB05 | EBGM | EB95 |
|---|---|---|---|---|---|---|
| PV DATABASE | 0 | | | | | |
| FAERS, PV DATABASE | 0 | | | | | |
| FAERS | 7221 | 20.15 | 125452.27 | 18.9 | 19.27 | 19.64 |

770

SOURCE CASE COUNT (SUMMARY)   704   762

▶ ANALYTICS DASHBOARD     LAST RUN: 05/11/2022 AT 14:10:00 EDT BY JANE DOE

FILTERS

▶ SOURCE
- □ ALL   708
- ☑ FAERS   709
- □ PV DATABASE   710

▶ REPORTING PERIOD
[01/01/2004] to [11/05/2022]

▶ SERIOUSNESS   712
- □ ALL   714

▶ FILTERS (5) CLEAR ALL FILTERS   774
- ≫ SOURCE: FAERS
- ≫ REPORTING PERIOD: 01/01/2004-11/05/2022
- ≫ SERIOUSNESS: RESULTS IN DEATH, LIFE THREATENING
- ≫ AGE GROUP: ADULT (18-65 YEARS), ELDERLY (65+ YEARS)
- ≫ GENDER: MALE

FILTERED SCORE SUMMARY

| SOURCE | CASE COUNT (N) | PRR | X2 | EB05 | EBGM | EB95 |
|---|---|---|---|---|---|---|
| FAERS | 2 | 3.76 | 4.05 | 0.56 | 1.67 | 4.1 |

SYSTEMS AND METHODS FOR ELECTRONICALLY COLLECTING AND LINKING STANDARDIZED CASE DATA IN A DATA WAREHOUSE

CROSS-REFERENCE TO RELATED APPLICATIONS

This application is a continuation of U.S. patent application Ser. No. 17/871,516, filed Jul. 22, 2022, which is incorporated herein by reference in its entirety.

TECHNICAL FIELD

The present disclosure relates to systems and methods for electronically collecting and linking standardized case datasets in a data warehouse.

BACKGROUND

Researchers, scientists, industry players, academics, government regulators, and other stakeholders are increasingly in need of a central source of standardized case data for determining and analyzing signals in the field of Pharmacovigilance.

SUMMARY

One embodiment relates to a method for determining a potential signal in a central case data storage system. The central case data storage system includes a provider computing system communicably coupled to a secure network. The provider computing system includes a central case data warehouse for storing one or more case data. The method includes receiving a request for case data and a statistical value minimum via the secure network. The method further includes selecting the case data from the central case warehouse based on the request and determining a statistical value based on the case data. The statistical value is at least one of: a case count, a proportional reporting ratio (PRR) value, a chi-squared value, an Empirical Bayes (EB) value, or an Interaction Singal Score (INTSS) value. The method further includes determining the potential signal associated with a specific adverse event code and a medical product identifier based on the statistical value and the statistical value minimum. The method further includes outputting the statistical value and the potential signal via the secure network.

Another embodiment relates to a method for determining a potential signal in a central case data storage system. The central case data storage system includes a provider computing system communicably coupled to a secure network. The provider computing system includes a central case data warehouse for storing one or more case data. The method includes receiving a request for case data and a statistical value minimum via the secure network. The method further includes selecting the case data from the central case warehouse based on the request and determining a statistical value based on the case data. The statistical value is at least one: an Empirical Bayes Geometric Mean (EBGM) value, an EB05 value, or an EB95 value. The method further includes determining the potential signal associated with a specific adverse event code and a medical product identifier based on the statistical value and the statistical value minimum. The method further includes outputting the statistical value and the potential signal via the secure network.

This summary is illustrative only and is not intended to be in any way limiting. Other aspects, inventive features, and advantages of the devices or processes described herein will become apparent in the detailed description set forth herein, taken in conjunction with the accompanying figures, wherein like reference numerals refer to like elements.

BRIEF DESCRIPTION OF THE FIGURES

FIG. 2 is a flow diagram of a method for electronically collecting and linking standardized case data in a data warehouse, according to an example embodiment.

FIGS. 7A-7B are illustrations of some aspects of a user interface generated by the standardized case dataset collection and signal detection system of FIG. 1 to analyze a specific potential signal, according to an example embodiment.

DETAILED DESCRIPTION

Figure 1:
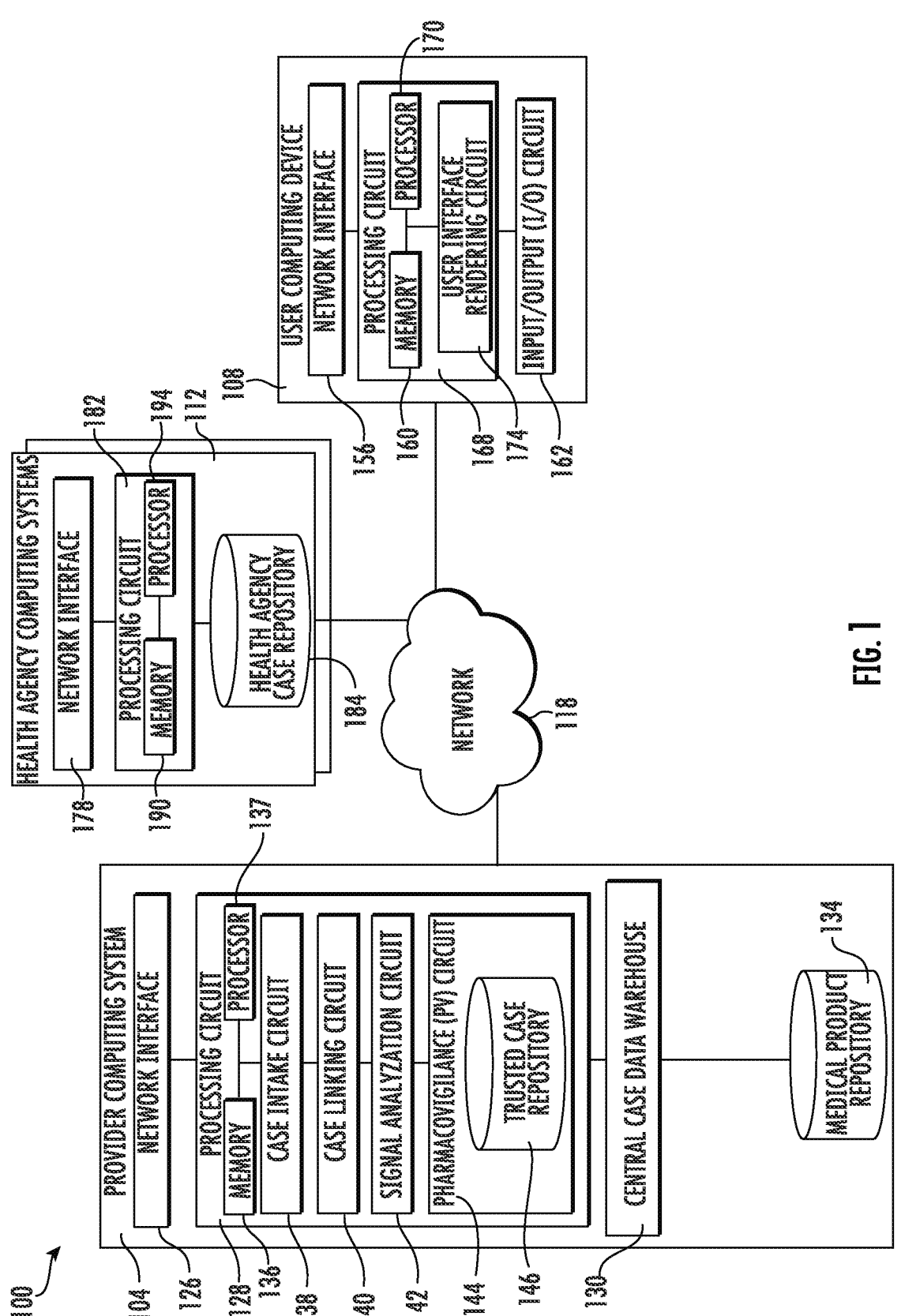
FIG. 1 is a component diagram of a standardized case dataset collection and signal detection system, according to an example embodiment.

Referring generally to the figures, systems and methods for electronically collecting and linking standardized case datasets in a data warehouse and detecting signals based on the linked case datasets are disclosed. The systems and methods described herein provide for higher quality and more available case data being stored within a central case data warehouse, which results in better quality signals and signal detection, thereby helping and improving the pharmacovigilance industry by more accurately and swiftly reporting signals to health authorities. For example, by standardizing received case data (and other additional case data) such that it is in a standard format, the present systems and methods can utilize multiple different data sources (including external sources) or repositories to collect case data for the central case data warehouse, which provides for more case data available when determining potential signals. In comparison, typical signal detection data management systems typically only utilize a single data source (e.g., so all the received case data is structured the same). As a result, the present systems and methods can more quickly and accurately determine potential signals and report the potential signals to health authorities. Further, by cleaning the case data by removing special characters and converting each field of the case data to a specific data type, the present systems and methods provide for a more reliable, trusted, and error-free data source, that can be used without having to handle and store invalid data. Because external case data can come from a variety of sources, the case data can typically include a large number of errors, invalid data, and be unreliable. In a typical signal detection data management system, these errors and invalid data may be stored within the case repository and utilized when detecting signals, which can provide or cause for inaccurate and unreliable signal detection. In comparison, the present systems and methods clean the case data by removing special characters, deduplicating the data, and converting each field of the case data to a specific data type which removes the errors and invalid data. By doing so, the central case data warehouse does not store the invalid data saving on memory and processing power and produces more valid and standardized case data which provides for more accurate and reliable signal detection overall.

Additionally, by determining matching portions (e.g., cases) of the received case data and then linking/merging the case data such that it is interconnected before outputting the case data, the present systems and methods output the maximum amount of case data possible while preventing duplicate cases from being included within the output case data, thereby providing an improvement to case data warehousing and querying systems and a technical solution to the technical problem of case duplication. For example, by preventing the output of duplicate case data by linking the case data and only outputting a single version of each case, the present systems and methods prevent duplicate bias which skews the signals and statistical values generated toward the duplicate data. Further, by outputting the case data based on a priority of the type of the case data, the present systems and methods select the maximum amount of case data that reflects the priority while not including duplicate cases. In typical case data warehousing and querying systems, a single data source is utilized such that linking/combining of the case data is not required, which provides for a much smaller set of case data. In comparison, by including the maximum amount of case data while still removing/preventing duplicate data, the present systems and methods provide for more accurate signal detection and overall better statistical values by including multiple sources/types of case data.

Additionally, by utilizing a central source of case data, the present systems and methods provide a single trusted data warehouse from which a wide variety of case data can be selected and output. In this regard, the present systems and methods use less processing power and memory by providing for a single central source of case data, as compared to typical case data systems. For instance, in typical case data systems, each type of case data may be stored separately in an individual location and then output from the individual location. In comparison, the present systems and methods utilize a single and central location that contains all of the case data. By doing so, the present systems and methods require less processing power to retrieve case data (e.g., by not having to determine which location(s) to retrieve data from) and memory with which to store the case data (e.g., by not having to replicate the same case in multiple separate locations).

As used herein, the term "event," "medical event," or "adverse event" can include any untoward medical occurrence which happens to either a patient or a subject in a clinical investigation or during regular use of a medical product that has been given to that person. For example, the "event," "medical event," or "adverse event" may encompass any signs which are unfavorable and unexpected for the patient or subject, including any abnormal laboratory findings such as a high blood pressure, a rapid heart rate, etc. The "event," "medical event," or "adverse event" could be symptoms, or a disease temporally associated with the use of a medical product and does not have to have been previously associated with that product. The term "event," "medical event," or "adverse event" can further encompass adverse reactions and serious adverse events such as death, life-threatening adverse experiences, inpatient hospitalization, congenital birth defects, disabilities, etc. Further, each "event," "medical event," or "adverse event" may be defined by the Medical Dictionary for Regulatory Activities (MedDRA) (or other medical event dictionaries) and associated with a specific MedDRA code. Moreover, "event information" "medical event information" "adverse event information" "event data" "medical event data" or "adverse event data" can include information associated with the event such as the date of onset of the event, the date of cessation of the event, the type of event, the dictionary term (e.g., MedDRA term), the dictionary code (e.g., MedDRA code), event comments, the outcome of the event, the location of the event (e.g., country where the event occurred), the event duration, patient data for a patient who endured or to which the event occurred, medical products that the patient consumed and/or dosages for the consumed medical products, the event rank, event contacts, the event type, and any associated event documents.

As used herein, the term "case" or "case dataset" can include an Individual Case Safety Report (ICSR) as defined by the standard ISO/HL7 27953 of the International Standards Organization (ISO) as well as any past or future standards governing ICSRs of the ISO, the World Health Organization (WHO), the Food and Drug Administration (FDA), the European Medicines Agency (EMA), or other national health agencies governing ICSRs. Moreover, "case information" "case data" or "case dataset" can include information associated with or included in the case such as adverse event data, case contact data, case priority data, case seriousness data, case documents, medical product registrations, patient data, and other data associated with a case as defined by the standard ISO/HL7 27953 as well as any past or future standards governing ICSRs of the ISO, the WHO, the Food and Drug Administration (FDA), the European Medicines Agency (EMA), or other national health agencies governing ICSRs.

As used herein, the term "signal" can include a signal as defined by the WHO, the FDA, the EMA, or other health agencies. Further, the term "signal" can include information on a new or known adverse event that is likely caused by a medical product and may be generated from more than a single case associated with the adverse event.

As used herein, the term "substance" can include a substance as defined by the WHO, the FDA, the EMA, or other health agencies. Further, the term "substance" can include an active ingredient or any component of a medical product that provides a pharmacological activity or other direct effect in the diagnosis, cure, mitigation, treatment, or prevention of disease, or to affect the structure or any function of the body of man or animals. In this regard, the "substance" may be a component responsible for the pharmacological activity of a medical product.

Additionally, as used herein the terms "information" and "data" may be used interchangeably such that one may be substituted for the other and vice versa.

Referring now to FIG. 1, a system 100 for electronically collecting and linking standardized case datasets in a data warehouse to determine one or more potential signals is shown, according to an example embodiment. The system 100 includes a provider computing system 104, one or more user computing devices 108, and multiple health agency or authority computing systems 112 connected by a secure network (e.g., a network 118).

The network 118 communicably and operably couples the provider computing system 104, the user computing devices 108, and the health agency computing systems 112 such that communicable and operable computing may be provided between the provider computing system 104, the user computing devices 108, and/or the health agency computing systems 112 over the network 118. In various embodiments, the network 118 includes any combination of a local area network (LAN), an intranet, the Internet, or any other suitable communications network, directly or through another interface.

The provider computing system 104 may be operated and managed by a provider (e.g., a software as a service (SaaS) provider, a cloud services provider, a software provider, a service provider, etc.) and may include a computer system (e.g., one or more servers (e.g., a cloud computing server) each with one or more processing circuits). In some embodiments, the provider computing system 104 may act as a host and provide an application (e.g., a web-based application, a mobile application, etc.) to each of the user computing devices 108 over the network 118 in response to authenticating the respective user computing device 108. As shown, the provider computing system 104 may include a network interface 126, a processing circuit 128, a central case warehouse 130, and a medical product repository 134. In some embodiments, the provider computing system 104 may include an input/output circuit (e.g., similar to or the same as an input/output circuit 162 that will be described further herein).

The network interface 126 is structured to establish connections with the user computing devices 108 and the health agency computing systems 112 by way of the network 118. The network interface 126 includes program logic and/or hardware-based components that connect the provider computing system 104 to the network 118. For example, the network interface 126 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 126 includes the hardware and machine-readable media structured to support communication over multiple channels of data communication (e.g., wireless, Bluetooth, near-field communication (NFC). In some embodiments, the network interface 126 includes cryptography logic and capabilities to establish a secure communications session.

Additionally, the network interface 126 may include AS2 gateway logic that includes programmable instructions that facilitate communication (transmission and receipt) using the AS2 Gateway communication protocol (as specified in Request for Comment (RFC) 4130) over the network 118 via the network interface 126. For example, using the AS2 gateway logic, the network interface 126 may transmit or receive electronic files (e.g., a source file including adverse event data, a case, a case dataset, etc.) or other data to the health agency computing systems 112 and/or the user computing devices 108 using the AS2 Gateway protocol.

The processing circuit 128, as shown, comprises a memory 136, a processor 137, a case intake circuit 138, a case linking circuit 140, a signal analyzation circuit 142, and a pharmacovigilance (PV) or case reporting circuit 144. The memory 136 includes one or more memory devices (e.g., RAM, NVRAM, ROM, flash memory, hard disk storage, etc.) that store data and/or computer code for facilitating the various processes described herein. That is, in operation and use, the memory 136 stores at least portions of instructions and data for execution by the processor 137 to control the processing circuit 128. The memory 136 may be or include tangible, non-transient volatile memory and/or non-volatile memory. The processor 137 may be implemented as a general-purpose processor, an application specific integrated circuit (ASIC), one or more field programmable gate arrays (FPGAs), a digital signal processor (DSP), a group of processing components, or other suitable electronic processing components.

The case intake circuit 138 is structured or configured to intake, clean (e.g., standardize, deduplicate, etc.), and manage case data received from one or more sources that may be provided to the provider computing system 104 (e.g., from the health agency computing systems 112). For example, the case intake circuit 138 may receive case data (e.g., health agency case data) associated with multiple cases from the health agency computing systems 112. Each case may be associated with a medical product and an adverse event. In response, the case intake circuit 138 may clean the health agency case data (e.g., remove unnecessary portions that take up memory, standardize the health agency case data, deduplicate the health agency case data, and the like), match or combine the health agency case data with medical product data of the medical product repository 134, and match the health agency case data with adverse event identifier(s) associated with one or more adverse events. For example, the case intake circuit 138 may determine the health agency case data includes a first National Drug Code (NDC) and the medical product data includes the same first NDC. In response, the case intake circuit 138 may combine the health agency case data associated with the first NDC and the medical product data associated with the first NDC. In some embodiments, the case intake circuit 138 may link or otherwise digitally connect (e.g., via an object pointer) the matching health agency case data and the medical product data. In another example, the case intake circuit 138 may determine the health agency case data includes a first adverse event code and the adverse event identifier is the same first adverse event code. In some embodiments, the case intake circuit 138 may link or otherwise digitally connect the matching health agency case data and the adverse event identifier. In response, the case intake circuit 138 may combine the health agency case data associated with the first adverse event and the adverse event identifier(s) associated with the first adverse event. Once the case data is cleaned and combined or matched with adverse event identifier(s) and medical product data, the case intake circuit 138 may store the case data within the central case warehouse 130 (e.g., within the one or more health agency repositories 131) and/or provide the case data to the case linking circuit 140.

The case linking or matching circuit 140 is structured or configured to receive the intaken (e.g., cleaned, standardized, deduplicated) case data from various sources, determine matching portions of the case data (e.g., cases), and link the matching portions. For example, the case linking circuit 140 may receive intaken health agency case data and trusted case data. The health agency case data may be associated with a first case and matched with a first medical product and a first adverse event and include first date/time data. Likewise, the trusted case data may be associated with a second case and include or be matched with a second medical product, a second adverse event, and include second date/time data. Then, by determining the first medical product is the same as the second medical product, the first adverse event is the same as the second adverse event, and the first date/time data is the same as the second date/time data, the case matching circuit 140 may determine the first case is a match with the second case (i.e., are the same case). In some embodiments, the case matching circuit 140 may determine the first case is a match with the second case (i.e., are the same case) based on a case identifier of the first case and the second matching (e.g., being the same). In some embodiments, for matching cases, the case linking circuit 140 may generate and include a link to the matched case within the respective case data. For instance and using the example above, the case linking circuit 140 may generate and include a link or other digital connection to the first case in the case data of the second case and vice versa. Once the link is generated and included in the case data associated with each of the respective cases, the case linking circuit 140 may store the case data in the central case warehouse 130 (e.g., within the one or more health agency repositories 131, within the one or more PV repositories 132, within the one or more additional case repositories 133, within the central case repository 195, etc.).

The signal analyzation circuit 142 is structured or configured to retrieve a specified set of case data from the central case warehouse 130 (based on one or more specified filters, sources, etc.) and analyze the specified set of case data for potential signals and statistical values. For example, the signal analyzation circuit 142 may determine one or more statistical values based on the case data. The statistical values may be provided to the user computing device 108. In response, the user computing device 108 may provide verification the potential signal is a signal or is not a signal. For instance, the signal analyzation circuit 142 may determine a first potential signal associated with the adverse event "Headache" and the medical product "Drug X" based on case data received from the central case warehouse 130. For instance, the signal analyzation circuit 142 may determine one or more statistical values (e.g., case count, disproportionality analysis values, etc.) such as a Proportional Reporting Ratio (PRR) statistical value, a chi-squared ($x^2$) test statistical value, and/or multiple Empirical Bayes (EB) statistical values. The signal analyzation circuit 142 may then provide the potential signal and/or the statistical values to the user computing device 108 for verification. In some embodiments, the signal analyzation circuit 142 may monitor the case data of the central case warehouse 130 for a change to a signal (e.g., new cases associated with the medical product and the adverse event, changes to the one or more statistical values, and the like). In some embodiments, the signal analyzation circuit 142 may store the signal and the one or more statistical values within a signal repository (not shown) of the provider computing system 104. In some embodiments, the signal analyzation circuit

142 may generate a signal data object associated with a medical product and an adverse event, in response to receiving a request to do so.

The (PV) or case reporting circuit 144 is structured or configured to intake adverse event data associated with a medical product and an adverse event (e.g., from the user computing device 108), generate a case, and output the case to the relevant health agencies. For example, the PV circuit 144 may receive adverse event data associated with "Drug X" and the adverse event "Headache". The PV circuit 144 may then process the adverse event data, generate a case including case data, and output the case to the health agency computing system 112 associated with the FDA. Further, the PV circuit 144 may include a trusted case repository 146 in which the cases and associated trusted case data are stored. In some embodiments, the PV circuit 144 may not output the case to the health agency computing systems 112, if not required. For example, the PV circuit 144 may determine the case does not require reporting to the FDA because it is a non-serious case. However, the PV circuit 144 may still store the case within the trusted case repository 146, making it available for signal detection and management.

The trusted case repository 146 is a repository (e.g., a database, cloud storage, etc.) that is structured or configured to receive, store, and manage case data associated with a medical product and adverse event of cases processed by the PV circuit 144. For example, the trusted case repository 146 may receive case data associated with a specific case dataset, a medical product, and an adverse event and store/manage the case data. In another example, the trusted case repository 146 may receive the case data and an associated data object (e.g., a case data object). For each case dataset stored within the trusted case repository 146, the trusted case repository 146 may further generate or receive/determine version data associated with each case dataset as well as date data indicating when the version of the case was active. For example, the trusted case repository 146 may receive a first case dataset on a first date and store the case dataset and associated case data within the trusted case repository 146 as version 1.0. Then, the trusted case repository 146 may receive a follow-up case dataset on a second date and combine the first case dataset with the follow-up case dataset. The trusted case repository 146 may store the combined case dataset within the trusted case repository 146 as version 2.0. In this example, the first version of the case was active from the first date to the second date, and the second version of the case was active from the second date on. The active dates may be used by the providing computing system 104 for retrieving case data from the central case warehouse 130 as will be described further herein.

Additionally, the trusted case repository 146 can be structured according to various database types, such as relational, hierarchical, network, flat, point-in time, and/or object relational. In some embodiments, the trusted case repository 146 includes a plurality of nonvolatile/non-transitory storage media such as solid-state storage media, hard disk storage media, virtual storage media, cloud-based storage drives, storage servers, and/or the like.

The trusted case repository 146 acts as a trusted or valid source of case data because of the quality of case data that is processed and generated by the PV circuit 144. For example, the PV circuit 144 typically receives adverse event data directly from the user computing device 108. Further, the PV circuit 144 may require multiple steps of validation and verification of the adverse event data before generating the case dataset.

Figure 9A:
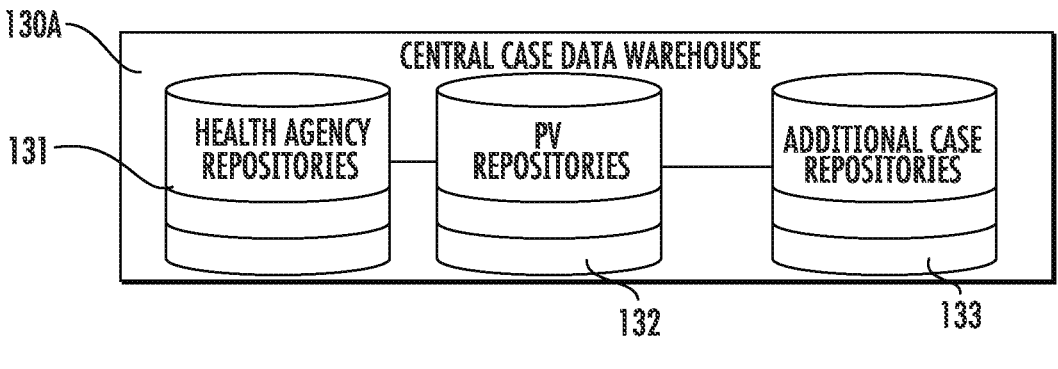
FIGS. 9A-9C are component diagrams of a central case data warehouse of the standardized case dataset collection and signal detection system of FIG. 1, according to an example embodiment.
Figure 9B:
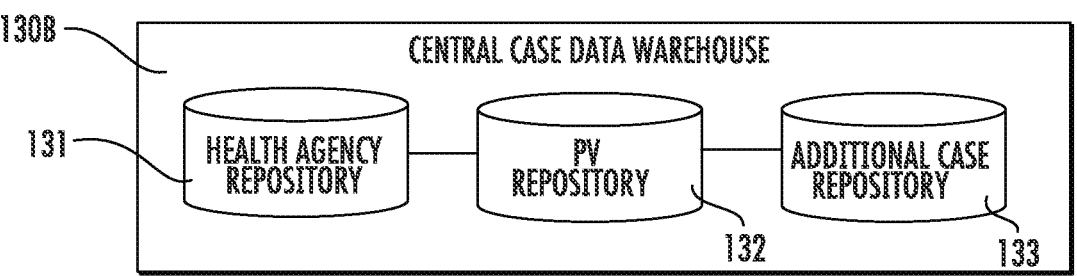
Figure 9C:
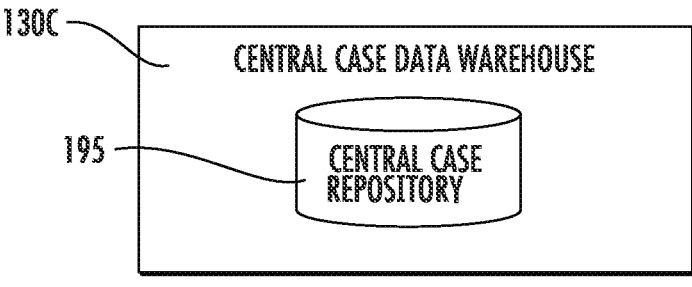

The central case warehouse 130 is one or more repositories (e.g., one or more databases, cloud storage, etc.) that are structured or configured to receive, store, and manage case data (e.g., trusted case data, health agency case data, external case data, etc) associated with one or more cases. For example, the central case warehouse 130 may receive trusted case data intaken and managed by the PV circuit 144, additional case data intaken by the case intake circuit 138, and health agency case data from the health agency case repository 184 intaken by the case intake circuit 138 and store/manage the case data therein. As shown in FIGS. 9A-9C and discussed further herein, the central data warehouse 130 may include one or more central health agency repositories 131, one or more central PV case repositories 132, and one or more additional case repositories 133. In some embodiments, the central data warehouse 130 includes a single central repository 195.

In some embodiments, the central case warehouse 130 may be a part of (e.g., included in) the processing circuit 128 and utilize the memory 136 and the processor 137 to perform the data operations described herein (e.g., intake, management). In other embodiments, the central case warehouse 130 may include a memory (e.g., similar or the same as the memory 136) and a processor (e.g., similar or the same as the processor 137) to perform the data operations described herein. The central case data warehouse will be described further herein within regard to FIGS. 9A-9C.

By being a central source of case data, the central case warehouse 130 provides a single trusted location from which a wide variety of case data can be selected and output. In this regard, the central case warehouse 130 reduces processing power and memory by providing for a single central source of case data, as compared to typical case data systems. For instance, in typical case data systems, each type of case data may be stored in separate locations and then output or requested from the individual location. In comparison, the central case warehouse 130 is a single central location which contains all of the case data. By doing so, the central case warehouse 130 and the provider computing system 104 require less processing power to retrieve case data (e.g., by not having to determine which location to retrieve data from) and memory with which to store the case data (e.g., by not having to replicate the same case in multiple locations and utilizing a single location for case data storage).

The medical product repository 134 is a repository (e.g., a database, cloud storage, etc.) that is structured or configured to receive, store, and manage medical product data associated with medical products (e.g., marketed drugs, marketed medical devices, etc.). For example, the medical product repository 134 may receive medical product data associated with a specific medical product (e.g., drug name, one or more substances included in the medical product, trade name, threshold statistical values associated with the medical product, a primary data source, identifiers (e.g., application number, NDC, etc.), medical product registration data (e.g., marketed medical product registrations for each country), associated clinical studies or trials, and the like) and store/manage the medical product data. In another example, the medical product repository 134 may receive the medical product data and an associated data object (e.g., a medical product data object). Further, the medical product repository 134 can be structured according to various database types, such as relational, hierarchical, network, flat, point-in time, and/or object relational. In some embodiments, the medical product repository 134 includes a plurality of nonvolatile/non-transitory storage media such as solid-state storage media, hard disk storage media, virtual storage media, cloud-based storage drives, storage servers, and/or the like.

In some embodiments, each different data or information type (e.g., case data, medical product data, adverse event data, signal data, substance data, etc.) may be stored in, and the provider computing system 104 may include a separate repository for each (not shown). For example, the provider computing system 104 may include a signal repository in which generated and/or verified signals (e.g., signal data objects) and associated signal data are stored. In another example, the provider computing system 104 may include an adverse event identifier repository or dictionary in which adverse event identifiers (e.g., a MedDRA term, a MedDRA code, associated MedDRA classes, etc.) are stored. Each repository may be similar to or structured the same as the medical product repository 134.

Still referring to FIG. 1, each of the one or more user computing devices 108 can be any type of computing device or computing system. For instance, each of the user computing devices 108 can be one or more of a mobile phone, a tablet computer, a laptop computer, a smart watch, a server computer system, or any other internet-connected device. In operation, the user computing devices 108 may communicate and interface with the provider computing system 104 via the network 118 to generate and provide a request to receive case data. For example, the user of one or more of the user computing devices 108 may interface with the provider computing system 104 to indicate the provider computing system 104 is to provide case data from any source within a first timeframe as well as determine potential signals based on the resulting case data. As shown, the user computing device 108 may include a network interface 156, a processing circuit 160, and the input/output (I/O) circuit 162.

The network interface 156 is structured to establish connections with the provider computing system 104 and/or the health agency computing systems 112 by way of the network 118. The network interface 156 includes program logic and/or hardware-based components that connect the user computing device 108 to the network 118. For example, the network interface 156 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 156 includes the hardware and machine-readable media structured to support communication over multiple channels of data communication (e.g., wireless, Bluetooth, near-field communication (NFC). In some embodiments, the network interface 156 includes cryptography logic and capabilities to establish a secure communications session.

The processing circuit 160, as shown, comprises a memory 168, a processor 170, and a user interface generation or rendering circuit 174. The memory 168 includes one or more memory devices (e.g., RAM, NVRAM, ROM, flash memory, hard disk storage, etc.) that store data and/or computer code for facilitating the various processes described herein. That is, in operation and use, the memory 168 stores at least portions of instructions and data for execution by the processor 170 to control the processing circuit 160. The memory 168 may be or include tangible, non-transient volatile memory and/or non-volatile memory. The processor 170 may be implemented as a general-purpose processor, an application specific integrated circuit (ASIC), one or more field programmable gate arrays (FP- GAs), a digital signal processor (DSP), a group of processing components, or other suitable electronic processing components.

The user interface generation or rendering circuit 174 may be configured to receive a user interface (e.g., a web interface in an HTML file and related files, a downloaded graphical user interface, etc.) from the provider computing system 104 and render the user interface on the user computing device 108 via the I/O circuit 162. In this way, the provider computing system 104 may generate one or more user interfaces and provide the one or more user interfaces to the user interface generation circuit 174 to be rendered on the user computing device 108 (e.g., on a display of the I/O circuit 162 of the user computing device 108).

The I/O circuit 162 is structured to receive communications from and provide communications to the user of one or more of the user computing devices 108 (e.g., the user). In this regard, the I/O circuit 162 is structured to exchange data with the processing circuit 160 to provide output to the user and to receive input from the user. As a result, the I/O circuit 162 may include a display that may be manipulated by the application. In some embodiments, the I/O circuit 162 may also include a keyboard, a mouse, a joystick, a touch screen, touch areas, soft keys, a microphone, a speaker, a vibration mechanism, a sensor, a RFID scanner, or other input or output devices described herein.

Still referring to FIG. 1, the health agency computing systems 112 can be any type of computing device or computing system and may be associated or managed by a health agency (e.g., the FDA, the EMA, Health Canada, etc.). For instance, at least one of the health agency computing systems 112 may be the Electronics Submission Gateway (ESG) of the FDA through which one or more E2B XML files and/or an FDA 3500A PDF files (e.g., case datasets) may be received from or provided to. In operation, each health agency computing system 112 may communicate with the provider computing system 104 or the user computing devices 108 to send and/or receive case data associated with case datasets (e.g., within E2B files). Further, the health agency computing system 112 is shown to include a network interface 178, a processing circuit 182, and a health agency case repository 184.

The network interface 178 is structured to establish connections with the provider computing system 104 and/or the user computing device 108 by way of the network 118. The network interface 178 includes program logic (e.g., AS2 Gateway logic) and/or hardware-based components that connect the health agency computing system 112 to the network 118. For example, the network interface 178 may include any combination of a wireless network transceiver (e.g., a cellular modem, a broadband modem, a Bluetooth transceiver, a Wi-Fi transceiver, a Li-Fi transceiver, etc.) and/or a wired network transceiver (e.g., an Ethernet transceiver). In some embodiments, the network interface 178 includes the hardware and machine-readable media structured to support communication over multiple channels of data communication (e.g., wireless, Bluetooth, near-field communication (NFC). In some embodiments, the network interface 178 includes cryptography logic and capabilities to establish a secure communications session.

The processing circuit 182, as shown, comprises a memory 190 and a processor 194. The memory 190 includes one or more memory devices (e.g., RAM, NVRAM, ROM, flash memory, hard disk storage, etc.) that store data and/or computer code for facilitating the various processes described herein. That is, in operation and use, the memory 190 stores at least portions of instructions and data for execution by the processor 194 to control the processing circuit 182. The memory 190 may be or include tangible, non-transient volatile memory, and/or non-volatile memory. The processor 194 may be implemented as a general-purpose processor, an application specific integrated circuit (ASIC), one or more field programmable gate arrays (FP-GAs), a digital signal processor (DSP), a group of processing components, or other suitable electronic processing components.

The health agency case repository 184 is a repository (e.g., a database, cloud storage, etc.) that is structured or configured to receive, store, and manage case data (e.g., health agency case data) associated with one or more cases. For example, the health agency case repository 184 may store and manage health agency case data received and processed by the health agency computing system 112. For instance, the health agency case repository 184 may be the FDA Adverse Event Reporting System (FAERS) which is a public database or repository that stores and manages portions of case datasets received by the FDA. In another example, the health agency case repository 184 may be the EMA's Eudra Vigilance System (EVDAS), the WHO's Vigibase, and the like. Further, the health agency case repository 184 can be structured according to various database types, such as relational, hierarchical, network, flat, point-in time, and/or object relational. In some embodiments, the health agency case repository 184 includes a plurality of nonvolatile/non-transitory storage media such as solid-state storage media, hard disk storage media, virtual storage media, cloud-based storage drives, storage servers, and/or the like.

Referring now to FIG. 2, a method 200 of electronically collecting and linking standardized case data in a data warehouse is shown, according to an example embodiment. Method 200 can be carried out by the system of FIG. 1. More particularly, the method 200 can be carried out by the processing circuit 128 of the provider computing system 104 and through communication with the user computing devices 108 and/or the health agency computing systems 112.

Method 200 commences at step 204 at which the provider computing system 104 receives health agency case data from one or more of the multiple health agency computing systems 112. The health agency case data may be associated with multiple cases, each case associated with a medical product and an adverse event. The health agency case data may include data pertaining to each of the cases including a medical product identifier (e.g., NDC product code, NDC package code, brand name, generic name, application number, substance name(s), drug authorization number, drug role, etc.) of the medical product associated with the case, an adverse event identifier (e.g., adverse event term, adverse event code, MedDRA version, etc.) of the adverse event associated with the case, a patient identifier (e.g., patient gender, patient age group, patient initials, etc.), a seriousness of the case (e.g., serious: results in death, serious: life threatening, non-serious, etc.), a case identifier (e.g., a case unique identifier (UID), a case ID, etc.), case version data, and/or one or more pieces of date/time data (e.g., date/time the case was first/initially received by the FDA, date/time the most recent case data was received by the health agency, etc.) associated with the case. In some embodiments, the health agency case data may be received from the health agency computing systems 112 (e.g., the FDA electronic submissions gateway) in a source document (e.g., an E2B XML file, etc.). In some embodiments, the health agency case data may be received from a specific health agency computing system 112 at a specific interval of time. For example, the provider computing system 104 may receive health agency case data from the health agency computing system 112 associated with the FDA every 3 months (because the FAERS releases updated data quarterly). In another example, the provider computing system 104 may receive health agency case data from the health agency computing system 112 associated with the EMA every month. In this regard, step 204 may repeat at an interval for each of the health agency computing systems 112.

Once the provider computing system 104 has received the health agency case data, the method 200 proceeds to step 208 at which the provider computing system 104 cleans the case data. To clean the health agency case data, the provider computing system 104 may remove special characters (e.g., "*", "_", characters that are not American Standard Code for Information Interchange (ASCII) characters, etc.) from the case data, remove duplicate cases within the health agency case data (e.g., based on the case identifier of each case matching, based on the reporting country of each case matching, based on the gender of each case matching, based on the event date of each case matching, based on the adverse events of each matching, and/or based on the medical product of each case matching), and/or standardize the health agency case data. For example, the provider computing system 104 may standardize the medical product identifiers (e.g., the medical product name or brand name) of the health agency case data by separating terms with multiple words (e.g., "Drugx (substancex)) into two separate medical product identifiers (e.g., "Drugx" and "substancex"). In another example, the provider computing system 104 may remove dosages, dosage forms, and route of administration (RoA) from the medical product identifier (e.g., "Drugx (300 MG)" to "Drugx" or "Drugx (tablet)" to "Drugx"). In another example, the provider computing system 104 may standardize the health agency case data by converting each field to a specific data type (e.g., patient age group to integers, drug name to a String, etc.)). In some embodiments to standardize the case data where multiple versions of a case are received by the provider computing system 104, the provider computing may generate a version active date and a version end date and add them to the health agency case data. For example, the provider computing system 104 may receive health agency case data for a case including a first version with a new information receipt date and/or initial receipt date of Jan. 1, 2001 and a second version with a new information receipt date of Jan. 1, 2002. In response, the provider computing system 104 may store the version data associated with each including determining and adding a version active start date/time of Jan. 1, 2001 and/or a version active end date/time of Jan. 1, 2002 for the first version and a version active start date/time of Jan. 1, 2002 and no version active end date/time for the second version of the case. In this regard, the version active start date is the new info date of the present version of the case, and the version active end date is the new info date of the next version of the case (assuming there is one).

Figure 4:
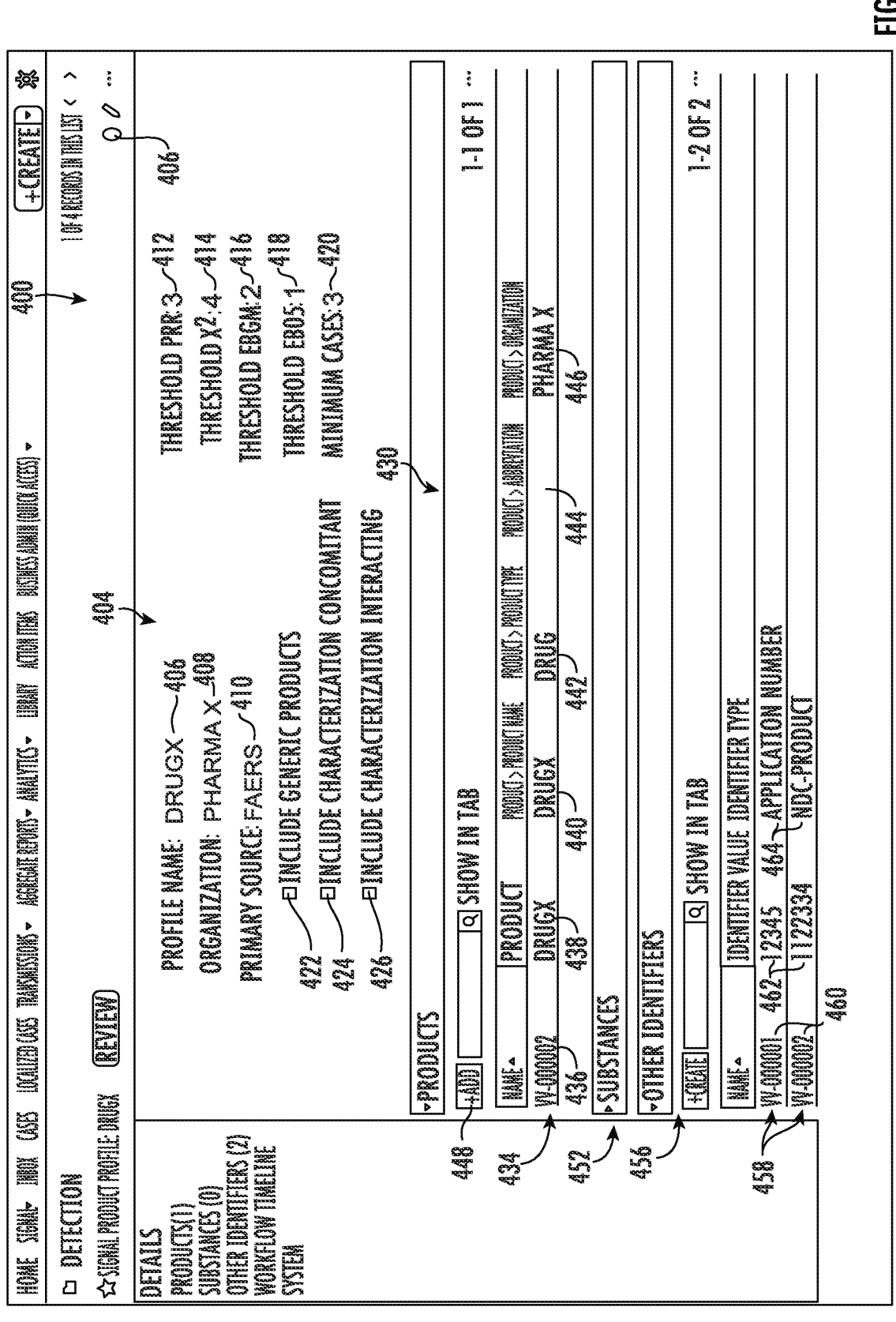
FIG. 4 is an illustration of some aspects of a user interface generated by the standardized case dataset collection and signal detection system of FIG. 1 to manage a signal product profile of one or more medical products, according to an example embodiment.

Once the provider computing system 104 has cleaned the health agency case data, the method 200 proceeds to step 210 at which the provider computing system 104 receives medical product data from the medical product repository 134 associated with one or more medical products. The medical product data may be received from the user computing device 108 and include data associated with multiple medical products (e.g., DrugX, DrugY, etc.). Further, for each medical product associated with the medical product data, the medical product data may include data pertaining to the medical product and signals associated with the medical product including a primary data source, a threshold PRR value, a threshold $x^2$ value, a threshold, EBGM value, a threshold EB05 value, a minimum number of cases, a customer or organization associated with the medical product, a name of the medical product, a medical product type, any substances included in the medical product, and one or more medical product identifiers (e.g., e.g., NDC product code, NDC package code, brand name, generic name, a medical product application number, substance name(s), drug authorization number, drug role, etc.) associated with the medical product. FIG. 4 shows a signal product profile page 400 through which the user of the user computing device 108 can generate and provide medical product data associated with one or more medical products to the provider computing system 104.

In some embodiments, at step 210, the provider computing system 104 may receive medical product data that is associated with a signal product profile (e.g., signal product profile data). The signal product profile may be associated with one or more medical products and include a name, one or more statistical value thresholds or minimums, a primary data source(s), an associated organization or customer, one or more associated substances, and one or more medical product identifiers, as shown and discussed regarding FIG. 4. In some embodiments, after receiving the signal product profile data, the provider computing system 104 may store the signal product profile in a signal product profile repository. In this regard, at or after step 210, the provider computing system 104 may retrieve or select the signal product profile from the signal product profile repository for subsequent use.

Once the provider computing system 104 has received the medical product data, the method 200 proceeds to step 211 at which the provider computing system 104 receives adverse event identifiers associated with one or more adverse events. In some embodiments, the adverse event identifiers may be received from a medical dictionary repository internal or external to the provider computing system 104 (e.g., a MedDRA repository (not shown)). Further, the adverse event identifier may include data pertaining to the adverse event such as an adverse event term (e.g., MedDRA term), adverse event code (e.g., MedDRA code), and/or the class within the MedDRA hierarchy of the adverse event (e.g., System Organ Class (SOC), High-Level Group Term (HLGT), High Level Term (HLT), Preferred Term (PT), Lowest Level Term (LLT), etc.). In some embodiments, each adverse event may be associated with two adverse event identifiers (e.g., a MedDRA term and MedDRA code).

In some embodiments, before or after step 211, the provider computing system 104 may receive data from one or more external repositories (not shown). For example, the provider computing system 104 may receive NDC data from an external NDC repository (e.g., the NDC directory associated with the FDA). The NDC data may include medical product data including multiple medical product identifiers (e.g., NDC product code, NDC package code, brand name, generic name, application number, substance name(s), drug authorization number, and/or drug role), a medical product marketing start date, and a medical product marketing end date. In another example, the provider computing system may receive substance data from an external substance repository (e.g., the Unique Ingredient Identifier (UNII) repository associated with the FDA). The substance data may include multiple substance identifiers (e.g., substance name, the chemical formula of the substance, UNII of the substance) and a list of marketed medical products within which the substance is used. In some embodiments, the provider computing system 104 may further receive Structured Product Labeling (SPL) data, RxNorm, data, and/or PharmClass data from external data repositories. The external data (e.g., the NDC data, the substance data, the SPL data, the RxNorm data, and/or PharmClass data) may be used by the provider computing system 104 to merge the health agency case data with the medical product data received at step 210 and/or the adverse event identifiers received at step 211. For example, the provider computing system 104 may utilize the external data to standardize vocabularies and determine matches between the medical product data, the adverse event identifiers, and/or the health agency case data.

Once the provider computing system 104 has received the adverse event identifiers, the method 200 proceeds to step 212 at which the provider computing system 104 combines the cleaned health agency case data with at least a portion of the medical product data and one or more of the multiple adverse event identifiers. To combine health agency case data with at least a portion of the medical product data, the provider computing system 104 may match at least a portion of the medical product identifiers of the medical product data with one or more medical product identifiers of the cleaned health agency case data. For example, the medical product data may be associated with a first case and a second case. As a result, the medical product data may include a first medical product identifier (e.g., an NDC) for the first medical product, a second medical product identifier for the second medical product (e.g., an NDC), and a third medical product identifier for the first medical product (e.g., an application number). The provider computing system 104 may search or analyze the cleaned health agency case data for any cases that include the first medical product identifier, the second medical product identifier, or the third medical product identifier. Then, in response to determining the cleaned health agency case data includes a case with the first medical product identifier, the provider computing system 104 may combine at least a part of the matching cleaned health agency case data with at least a part of the matching medical product data. For instance, if the cleaned health agency data includes an NDC but does not include substance data and a brand name, the provider computing system 104 may add the substance data and the brand name of the medical product data to the cleaned health agency data and generate combined cleaned health agency data.

Likewise, to combine health agency case data with one or more of the adverse event identifiers, the provider computing system 104 may match at least a portion of the adverse event identifiers with one or more adverse event identifiers of the cleaned health agency case data. For example, the adverse event identifier may be associated with a first adverse event. As a result, the adverse event identifiers may include a first adverse event identifier (e.g., a MedDRA term) for the first adverse event and a second adverse event identifier for the first adverse event (e.g., a MedDRA code). The provider computing system 104 may search or analyze the cleaned health agency case data for any cases that include the first adverse event identifier or the second adverse event identifier. Then, in response to determining the cleaned health agency case data includes a case with the first adverse event identifier, the provider computing system 104 may combine at least a part of the matching cleaned health agency case data with at least a part of the matching adverse event identifier(s). For instance, if the cleaned health agency data includes a MedDRA term but does not include a MedDRA code, the provider computing system 104 may add the MedDRA code of the adverse event identifier(s) to the cleaned health agency data and generate combined health agency data.

In some embodiments, to combine the cleaned health agency case data with the medical product data and generate or determine combined health agency case data, the provider computing system 104 may further include a link to a medical product data object of the medical product data within the combined health agency case data. For example, the provider computing system 104 may determine the cleaned health agency case data includes case data associated with a first medical product, and that the medical product data includes medical product data associated with the first medical product. In response, the provider computing system 104 may combine the matching medical product data with the matching health agency case data and generate combined health agency case data including a link or other digital connection (of the medical product data) to a medical product data object associated with the medical product.

In some embodiments, to combine the cleaned health agency case data with the adverse event identifiers and generate or determine combined health agency case data, the provider computing system 104 may further include a link to an adverse event identifier data object of the adverse event identifier within the combined health agency case data. For example, the provider computing system 104 may determine the cleaned health agency case data includes case data associated with a first adverse event, and that the adverse event identifier includes an identifier matching the first adverse event In response, the provider computing system 104 may combine the matching adverse event identifier with the matching health agency case data and generate combined health agency case data including a link or other digital connection to an adverse event identifier object associated with the adverse event.

In some embodiments, the provider computing system 104 may use the external data to combine the cleaned health agency case data with at least a portion of the medical product data and the adverse event identifiers. For instance, if the provider computing system 104 combines or codes all the cases within the case data with medical product data and adverse event identifiers besides two (e.g., a first case and a second case), the provider computing system 104 may use the external data to assist in combining the data. For example, the case data associated with the first case may have been combined or matched with the adverse event identifier but not a medical product. In response, the provider computing system 104 may utilize the external data (e.g., the NDC data, the substance data, the SPL data, the RxNorm data, and/or PharmClass data) to transform the medical product identifier of the case data to one that matches the medical product data. For instance, the NDC data may include an NDC product code that matches the NDC product code of the cleaned health agency case data and is not included within the medical product data. Then, the provider computing system 104 may determine a medical product identifier (e.g., brand name) of the cleaned health agency case data based on the NDC data, and match/combine the cleaned health agency case data with the medical product based on the determined medical product identifier.

By cleaning the health agency case data received from the health agency case repository 184 (and other additional case data) and then combining the health agency case data with the medical product data from the medical product repository 134 and the adverse event identifiers of the adverse event identifier repository (not shown) such that the resulting case data is a standard format, standard data type, and deduplicated, the provider computing system 104 provides for higher quality and more available case data stored within the central case data warehouse 130 and a technical improvement to signal detection data management systems overall. For example, because the provider computing system 104 standardizes the health agency case data (and other additional case data) and combines the case data with medical product data and adverse event identifiers such that it is in a standard format, the provider computing system 104 is able to utilize multiple different data sources (including external sources) or repositories to collect case data for the central case data warehouse 130, which provides for more case data available to the provider computing system 104 when determining potential signals than in typical signal detection data management systems, which typically only utilize a single data source (e.g., so all the received case data is structured the same). Further, because the provider computing system 104 cleans the case data by removing special characters and converting each field of the case data to a specific data type, the provider computing system 104 and the central case data warehouse 130 provide for a more reliable, trusted, and error-free data source, that can be used without having to handle and store invalid data. Because external case data can come from a variety of sources, the case data can typically include a large number of errors, invalid data, and be unreliable. In a typical signal detection data management system, these errors and invalid data may be stored within the case repository and utilized when detecting signals, which can provide or cause inaccurate and unreliable signal detection. In comparison, the provider computing system 104 cleans the case data by removing special characters, deduplicating the data, and converting each field of the case data to a specific data type which removes the errors and invalid data. By doing so, the central case data warehouse 130 does not store the invalid data saving on memory and processing power and produces more valid and standardized case data which provides for more accurate and reliable signal detection overall.

Once the provider computing system 104 has combined the cleaned health agency case data with at least a portion of the medical product data and at least a portion of the adverse event identifiers and generated/determined combined health agency case data, the method 200 proceeds to step 216 at which the provider computing system 104 receives or selects trusted case data from the trusted case repository 146. The trusted case data may be associated with multiple cases, each case associated with a medical product and an adverse event. The trusted case data may include data pertaining to each of the cases including a medical product identifier (e.g., NDC product code, NDC package code, brand name, generic name, application number, substance name(s), drug authorization number, drug role, etc.) of the medical product associated with the case, an adverse event identifier (e.g., adverse event term, adverse event code, MedDRA version, etc.) of the adverse event associated with the case, patient non-identifying data (e.g., patient initials, patient age group, patient gender, etc.), adverse event information associated with the case (e.g., reporter country, reporter qualification, etc.), a seriousness of the case (e.g., serious: results in death, serious: life threatening, non-serious, etc.),), a case identifier (e.g., a case unique identifier (UID), a case ID, etc.), case version data (e.g., version 1.0, version active start date, version active end date), and/or one or more pieces of date/time data (e.g., date/time the case was first/initially received by the PV circuit 144, date/time the most recent case data was received by the PV circuit 144, etc.) associated with the case. In some embodiments, the trusted case data may be received or selected from the trusted case repository 146 before the health agency case data (e.g., before step 204). In some embodiments, the trusted case data may be received by the provider computing system 104 at a specific interval of time (e.g., weekly). In other embodiments, the trusted case data may be received by the provider computing system 104 as the cases enter a closed state (e.g., closed, submitted, etc.) as determined by the PV circuit 144. For example, the PV circuit 144 may change the state of a specific case from Active to Closed and then provide the case and the trusted case data to the central case data warehouse 130 for storage (e.g., within the one or more PV repositories 132).

By utilizing the trusted case repository 146 and receiving trusted or PV case data, the provider computing system 104 and the system 100 provide for an improved signal detection system overall. For instance, typical signal detection systems may utilize a single source of case data (e.g., FAERS) to determine and detect potential signals, which can lead to a shortage in data as well as missing or not including cases that are determined to not require reporting to the health authority (e.g., the FDA). In comparison, the present system 100 is a signal detection system that directly receives trusted case data from the PV circuit 144 (e.g., from a PV safety application). By doing so, the system 100 and the provider computing system 104 has access to case data that is not reported to the health authorities but still may provide helpful insights and more accurate signals overall. Further, because the case data is received from the trusted case repository 146 and the PV circuit 144, the case data is assumed to be of a high quality and accuracy (e.g., due to the rigors the case data must go through in the PV circuit 144 (e.g., validation, verification, medical review, etc.) and does not require cleaning while still being relatively error free. As a result, the provider computing system 104 saves on processing power by not cleaning the trusted case data, while still storing a high-quality and valid set of case data within the central case data warehouse 130 and then utilizing the trusted set of case data to determine potential signals.

In some embodiments, the order in which the medical product data, the adverse event identifiers, the trusted case data, and the health agency case data are received may differ from what is shown (e.g., the adverse event identifiers may be received before the medical product data and the health agency case data, the trusted case data may be received before health agency case data, and the like). Furthermore, in some embodiments, medical product data, the adverse event identifiers, the trusted case data, and/or the health agency case data may be received in two or more steps. For example, the provider computing system 104 may receive a first set of health agency case data at step 204 (and proceed through steps 204-212) and a second set of health agency case data at a later time (and again proceed through steps 204-212). In this regard, the provider computing system 104 may receive the medical product data, the adverse event identifiers, the trusted case data, and/or the health agency case data as a stream of data in portions over time. When the provider computing system 104 receives multiple sets of case data, the provider computing system 104 may move through the order of the method 200 in the same way. If for example, the provider computing system 104 receives a set of trusted case data but does not receive a set of health agency case data, the provider computing system 104 may begin at step 216 and match/combine the trusted case data with the case data included in the central case data warehouse 130 (e.g., within the one or more health agency repositories 131, within the one or more PV repositories 132, and/or within the one or more additional case repositories 133) at step 220. Likewise, if the provider computing system 104 receives a set of health agency case data but does not receive a set of trusted case data, the provider computing system 104 may begin at step 204 and match/combine the trusted case data with the case data included in the central case data warehouse 130 (e.g., within the one or more health agency repositories 131, within the one or more PV repositories 132, and/or within the one or more additional case repositories 133) at step 220 (and skip step 216). In this regard, the provider computing system 104 may link or match the case data incrementally (as it is received).

Once the provider computing system 104 has received the trusted case data, the method 200 proceeds to step 220 at which the provider computing system matches at least a portion of the combined health agency case data with the trusted case data (e.g., determines the portions match). To match each case of the combined health agency case data with the trusted case data, the provider computing system 104 may determine whether each case of the trusted case data matches a case of the combined health agency data based on the case identifier being the same. For example, the provider computing system 104 may determine the trusted case data is associated with a first case and includes a first case identifier (e.g., case UID "101"). Then, the provider computing system may search the combined health agency data for a case including the same first case identifier and determine one or more matches. In some embodiments, at step 220, the provider computing system 104 may match one or more of the cases of the trusted case data and the combined health agency case data (e.g., based on matching case identifiers). Then, after step 220, the provider computing system 104 may link the case data and the combined health agency case data based on the matching cases.

In some embodiments and in response to determining a match, the provider computing system 104 may generate a link or other digital connection and modify the trusted case data to include the link. The link may point to the matching case of the combined health agency case data and provide an indication that each case is the same. Likewise, the provider computing system 104 may generate a second link or other digital connection and modify the combined health agency case data to include the second link. The second link may point to the matching case of the trusted case data and provide an indication that each case is the same. In other embodiments, the provider computing system 104 may join/combine the trusted case data and the combined health agency case data into a single set of central case data (e.g., within a single table) into which each case is distinct. For example, the provider computing system 104 may generate a set of central case data including or associated with multiple cases. In some embodiments, the central case data may be stored in a table. As a result, each case may be delimited by a separate row or column and/or each case electronic data source or case data type (e.g., PV circuit 144, a first health agency computing system 112, a second health agency computing system 112) is delimited by a separate row or column. In this regard, while the case data is combined or mixed to form the central case data, each type or source of case data (e.g., trusted case data, health agency case data, etc.) is still distinguished and/or separated, such that the provider computing system 104 can output each type of case data individually.

In some embodiments, prior to step 220, the provider computing system 104 may receive additional case data (e.g., external case data). For example, the provider computing system 104 may receive additional case data from a medical literature repository (e.g., PubMed®, Embase®, and the like), a social media case mining repository (i.e., a repository where potential or verified cases that are mined from social media (e.g., Facebook®, Twitter®, etc.) data are stored), and other external repositories through which case data can be retrieved/received from. Moreover, at step 220, the provider computing system 104 may match and/or combine the trusted case data, the combined health agency case data, and the additional case data based on the case identifiers of each. For instance, the provider computing system 104 may match a first case of the trusted case data, with a second case of the combined health agency case data and a third case of the additional case data based on each having the same case identifier (e.g., case UID). The provider computing system 104 may then combine/join or link all of the matching case data as described herein. In some embodiments, the provider computing system 104 may further assign a priority ranking to each electronic data source. For example, the provider computing system 104 may assign a priority of 1 to the trusted case data source, a ranking of 2 to the health agency case data source, and the like.

While multiple types of case data are described herein, it should be understood that each type of case data (e.g., central case data, health agency case data, trusted case data, external social media case data, external medical literature case data, etc.) is associated with or includes data that is related to a case. While the different types of case data may be structured differently overall, each type of case data may include a case identifier, a medical product identifier, an adverse event identifier, and/or date data. If the case data received does not include one or more of a case identifier, a medical product identifier, an adverse event identifier, and/or date data, the provider computing system 104 may clean and combine the case data as discussed with regard to step 208 and 212 to standardize the case data and ensure all the case data stored within the central case data warehouse 130 is usable.

Once the provider computing system 104 has matched and linked or combined the trusted case data and the combined health agency case data, the method 200 proceeds to step 224 at which the provider computing system 104 stores the combined health agency case data and the trusted case data within the central case data warehouse 130 (e.g., within the one or more health agency repositories 131 and within the one or more PV repositories 132). In some embodiments, the provider computing system 104 may store the generated central case data within the central case data warehouse 130 (e.g., within he central case repository 195) at step 224. In one example, the central case data may be stored within a table and the table may be stored within the central case repository 195 of the central case data warehouse 130.

Once the provider computing system 104 has stored the case data (e.g., the central case data) within the central case data warehouse 130, the method 200 proceeds to step 228, at which the provider computing system 104 receives a request for case data. The request may identify one or more electronic sources (electronic data sources) (e.g., the trusted case repository 146, FAERs, one or more external medical literature case repositories, EVDAS, etc.). In some embodiments, the request for case data may be generated by and received from the user computing device 108.

If at step 228 the request identifies only the health agency case repository 184 as the electronic data source, the method

200 proceeds to step 232, at which the provider computing system 104 outputs the combined health agency case data (e.g., from the health agency repository 131). In some embodiments, if the different types of case data were combined to form central case data, the provider computing system 104 may output the portion of the central case data delimited as from the health agency case repository 184 (e.g., the portion of the central case data within the health agency case repository 184 row or column) from the central case repository 195. In some embodiments, the combined health agency case data may be output by the provider computing system 104 to the user computing device 108 (e.g., to enable display on a user interface as will be described further herein.). In other embodiments, the combined health agency case data may be output by the provider computing system to one or more of the health agency computing systems 112. In some embodiments, the request may include an address (e.g., IP address, email address, Amazon S3® bucket address, file transfer protocol (FTP) address, etc.) to which the case data is to be output.

If at step 228 the request identifies only the trusted case repository 146 as the electronic data source, the method 200 proceeds to step 236, at which the provider computing system 104 outputs the trusted case data (e.g., of the one or more PV repositories 132). In some embodiments, if the case data was combined to form central case data, the provider computing system 104 may output the portion of the central case data delimited as from the trusted case repository 146 (e.g., the portion of the central case data within the trusted case repository 146 row or column) from the central case repository 195. In some embodiments, the trusted case data may be output by the provider computing system 104 to the user computing device 108 (e.g., to enable display on a user interface as will be described further herein.) In other embodiments, the trusted case data may be output by the provider computing system to one or more of the health agency computing systems 112. In some embodiments, the request may include an address (e.g., IP address, email address, Amazon S3® bucket address, file transfer protocol (FTP) address, etc.) to which the case data is to be output.

If at step 228 the request identifies both the health agency case repository 184 and the trusted case repository 146 as the electronic data sources, the method 200 proceeds to step 240, at which the provider computing system 104 outputs the trusted case data (e.g., from the PV repositories 132) and a portion of the combined health agency case data (e.g., from the health agency repository 131). As described herein, because the trusted case repository 146 is an internal repository to the provider computing system 104 and receives high-quality case data, the trusted case repository 146 is trusted or preferred. In this regard and when both electronic sources are selected, the provider computing system 104 may output the trusted case data and the portion of the combined health agency case data for which there is no matching trusted case data. By doing so, the provider computing system 104 outputs the highest relative quality of case data, while providing for maximum volume of case data. The provider computing system 104 may determine the combined health agency case data for which there is no matching trusted case data based on the links included in the health agency case data. In some embodiments, the portion of the combined health agency case data for which there is no match and the trusted case data may be output by the provider computing system 104 to the user computing device 108 (e.g., to enable display on a user interface as will be described further herein.) In other embodiments, the portion of the combined health agency case data for which there is no match and the trusted case data may be output by the provider computing system to one or more of the health agency computing systems 112. In some embodiments, the request may include an address (e.g., IP address, email address, Amazon S3® bucket address, file transfer protocol (FTP) address, etc.) to which the case data is to be output.

To output the trusted case data and the portion or segment of the combined health agency data, the provider computing system 104 may first select or query the central case warehouse 130 for all case data associated with the medical product (e.g., all of the combined health agency case data from step 232 and all of the trusted case data from step 236). Then, the provider computing system 104 may determine the matching portion or segment of the combined health agency case data based on the generated links included in the selected trusted case data. Finally, the provider computing system 104 may remove the matching portion or segment of the combined health agency case data from all of the selected health agency case data. The resulting portion or segment may be the health agency case data for which there is no match.

In some embodiments, if the case data was combined to form central case data, the provider computing system 104 may output the portion of the central case data delimited as from the trusted case repository 146 and the portion of the central case data delimited as from the health agency case repository 184 for which there is no match (e.g., for which there is no data in the trusted case repository row or column).

In some embodiments, when more than one electronic data source is identified in the request, the provider computing system 104 may select portions of the central case data based on the priority of each electronic data source. For example, if the request identifies the health agency case repository 184, the trusted case repository 146, and an external medical literature case repository, the provider computing system 104 may output portions of each case type based on the priority of the electronic data source. If, for example, the trusted case repository 146 was assigned priority 1, the health agency case repository 184 was assigned priority 2, and the external medical literature case repository was assigned priority 3, the provider computing system 104 may output all of the trusted case data that matches the request, the combined health agency case data for which there is not a match with the trusted case data, and the medical literature case data for which there is not a match with the trusted case data or the combined health agency case data. In some embodiments, because the trusted case repository 146 is trusted or preferred, the trusted case repository 146 may always be assigned a priority of 1, and the user computing device 108 may assign a priority to the rest of the electronic data sources. In other embodiments, the user computing device 108 may assign a priority to all of the electronic data sources. In some embodiments, if there are multiple versions of a case that match the request (e.g., version 1.0 from the trusted case repository 146, version 2.0 from the trusted case repository 146, and version 2.0 from the health agency case repository 184), the provider computing system 104 may output the most recent version of the case from the highest priority source.

By linking or merging the case data such that it is interconnected and then outputting the case data based on the electronic data source(s) of the request, the provider computing system 104 outputs the maximum amount of case data possible while preventing duplicate cases from being included within the output case data, thereby providing an improvement to case data warehousing and querying systems. For instance, by outputting the case data based on the priority of the type of the case data, the provider computing system 104 selects the maximum amount of case data that reflects the priority (e.g., as much case data as possible from the source identified as priority 1, any case data that is not available from priority 1 from the source identified as priority 2, and so on) while not including duplicates. In typical case data warehousing and querying systems, a single data source is utilized such that linking/combining of the case data is not required, which provides for a much smaller set of case data. In comparison, by including the maximum amount of case data while still removing/preventing duplicate data, the provider computing system 104 provides for more accurate signal detection and overall better statistical values by including multiple sources/types of case data. The additional case data provides for more insights and data points on which the provider computing system 104 can calculate the statistical scores and determine potential signals, thereby providing more accurate signal detection. Further, by preventing the output of duplicate case data by linking the case data and only outputting a single set of each case, the provider computing system 104 prevents duplicate bias which skews the signals and statistical values generated toward the duplicate data.

Additionally, by linking or combining each type of the case data such that it is still distinguishable and can be individually output, the provider computing system 104 provides for a central repository and location of case data while providing flexibility and customizability on the case data sought. In this regard, the provider computing system 104 allows for the user computing device 108 to indicate (e.g., in the request) the sources from which case data is sought, and the provider computing system 104 outputs the corresponding case data while preventing duplicates from being output. By doing so, the provider computing system 104 provides additional insights into the signal and statistical values that are typically not available due to the use of a single source by separating the case data based on the source.

Figure 3:
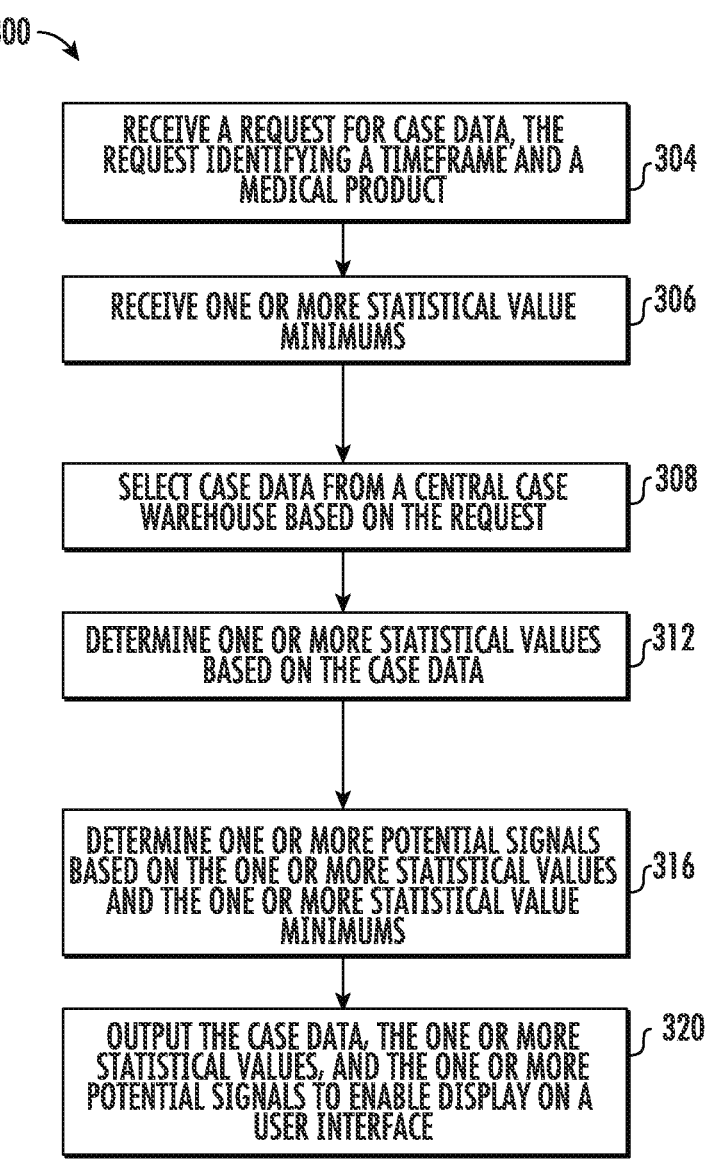
FIG. 3 is a flow diagram of a method of dynamically querying standardized case data from a data warehouse and determining one or more potential signals, according to an example embodiment.

Referring now to FIG. 3, a method 300 of dynamically querying standardized case data from the data warehouse and determining one or more potential signals is shown, according to an example embodiment. While different overall, it should be understood that any steps or discussion of the method 300 may be applied or included within the method 200, and vice versa, and that such combinations are included within the scope of the present disclosure. For example, the method 300 may include any of the steps 204-240, after or before any steps included in the method 300, and the method 200 may include any of the steps 304-328, after or before any of the steps included in the method 200. In this regard, method 200 demonstrates how the case data may be standardized and loaded into the central case data warehouse 130, and the method 300 demonstrates how the case data may be queried and output from the central case data warehouse 130. Method 300 can be carried out by the system of FIG. 1. More particularly, the method 300 can be carried out by the processing circuit 122 of the provider computing system 104 and through communication with the user computing device 108 and the health agency computing systems 112.

Method 300 commences at step 304 at which the provider computing system receives a request for case data. The timeframe may include a start date/time and an end date/time. The request may identify a timeframe and a medical product. In some embodiments, the request may further identify an electronic data source, an adverse event, and one or more filters (e.g., statistical value minimums or maximums, age group(s), gender(s), seriousness, etc.) as will be described further herein. In some embodiments, the request may be received from and generated by the user computing device 108. In some embodiments, the request may include an electronic address to which the resulting case data is to be provided.

Once the provider computing system 104 has received the request, the method 300 proceeds to step 306 at which the provider computing system 104 receives one or more statistical value minimums or thresholds. In some embodiments, the statistical value thresholds may be received within the medical product data (e.g., of step 210 of the method 200) from the user computing device 108. In other embodiments, the statistical value thresholds may be received as a part of a signal product profile (e.g., signal product profile data). The statistical value minimums may represent a minimum value for each of the statistical values when determining potential signals of the medical product. For instance, the statistical value minimums received in association with Drugx, may indicate a potential signal of Drugx must have a minimum of 3 cases and a minimum PRR of 3. In other embodiments, the statistical value minimums may be received separately from the medical product data and be specific to all medical products. In some embodiments, the statistical value minimums may be specific to a selected adverse event.

Once the provider computing system 104 has received the statistical value minimums, the method 300 proceeds to step 308 at which the provider computing system 104 selects case data from the central case warehouse 130 (e.g., from the one or more health agency repositories 131, from the one or more PV repositories 132, from the one or more additional case repositories 133, etc.) based on the request. For example, the provider computing system 104 may query or select case data from the central case warehouse 130 based on the case data matching or including the medical product identified in the request (e.g., based on a medical product identifier of the case data matching a medical product identifier of the case data). In addition, the provider computing system 104 may query or select case data based on the case data being active within the timeframe (e.g., after the start date/time and before the end date/time of the case data). For instance, the request may request and/or identify case data associated with DrugX that was active between Jan. 1, 2001 and Jan. 1, 2002. In response, the provider computing system 104 may query or select case data that is associated with or includes DrugX and that includes a receipt or new info date/time (e.g., an active version start date/time) before Jan. 1, 2002 and an active version end date/time after Jan. 1, 2001. If two or more versions of the same case meet this criterion, the provider computing system 104 may select the most recent version from the central case warehouse 130 (e.g., from the one or more health agency repositories 131, from the one or more PV repositories 132, from the one or more additional case repositories 133, etc.).

In some embodiments, the request may identify a signal product profile (which will be described further herein); each signal product profile may represent or be associated with multiple medical products (e.g., DrugX (50 mg) and DrugX (30 mg)) or substances. In this regard, at step 308, the provider computing system 104 may return case data that matches the signal product profile (e.g., either DrugX (50 mg) or DrugX (30 mg)).

If the request further includes or identifies an adverse event and one or more filters, the provider computing system 104 may further query or select case data from the central case warehouse 130 (e.g., from the one or more health agency repositories 131, from the one or more PV repositories 132, from the one or more additional case repositories 133, etc.) based on the case data meeting/matching the adverse event and the one or more filters (in addition to the medical product and the timeframe). For example, if the request further identifies an adverse event of "stomach mass" and a filter of seriousness being "Results in Death", the provider computing system 104 may select case data of cases in which the adverse event is a stomach mass (e.g., based on the adverse event identifiers matching) and the seriousness is results in death. If the request further includes or identifies one or more electronic data sources, the provider computing system 104 may select the case data as described with reference to the steps 228-240 of the method 200 from the central case warehouse 130 (e.g., based on the priority and the matching case data as determined by the provider computing system 104 at step 220).

As described herein, the central case data warehouse 130 may include one or more health agency repositories 131, one or more central PV case repositories 132, and one or more additional case repositories 133. In this regard, the case data selected at step 308 may be selected, by the provider computing system (e.g., the processing circuit 128), from any of the one or more health agency repositories 131, the one or more additional case repositories 133, and the one or more central PV case repositories 132 of the central case data warehouse 130. For instance, the provider computing system 104 may query or select case data from the central health agency case repository 131 and one or more of the multiple central PV case repositories 132 based on the case data matching or including the medical product identified in the request. As described herein, each central PV case repository 132 may be associated with and include trusted case data associated with a specific medical product. In this regard, the provider computing system may query or select case data from a specific PV repository 132 based on the case data matching or including the medical product identified in the request.

Once the provider computing system 104 has selected the case data from the central case data warehouse 130, the method 300 proceeds to step 312 at which the provider computing system 104 determines one or more statistical values based on the selected case data. If the request does not specify an adverse event, the provider computing system 104 may determine one or more statistical values for each MedDRA PT adverse event within the case data. For instance, the provider computing system 104 may group the selected case data by PT and determine one or more statistical values including a case count, a PRR value, an $x^2$ value, multiple EBGM values, an Interaction Signal Score (INTSS) value, one or more confidence scores, and/or the like for each group of cases/case data. In comparison, if the request specifies an adverse event, the provider computing system 104 may determine one or more statistical values for the case data associated with that adverse event.

The PRR value is a statistical value that is used to summarize the extent to which a particular adverse event is reported for individuals taking a specific medical product, compared to the frequency at which the same adverse event is reported for patients taking some other medical product. A PRR value greater than 1 typically suggests that the adverse event is more commonly reported for individuals taking the medical product of interest, relative to the comparison medical product. Similarly, the $x^2$ value is a statistical test and value that is produced and used to determine whether there is a statistically significant difference between the expected frequencies and the observed frequencies of adverse events occurring with the use of a medical product. Standard values of interest for PRR are >=3 and >=4 for $x^2$, with >=3 cases.

The EB values include the Empirical Bayes Geometric Mean (EBGM) value, the EB05 value, and the EB95 value. The EB values are calculated using the Multi-Item Gamma Poisson Shrinker (MGPS) method, where a repository or a combination of repositories is analyzed and searched for the occurrence of unexpectedly frequent medical product-event combinations occurring. MGPS produces a score called EBGM, EB05, and EB95 for a medical product-adverse event combination and a score called INTSS for a medical product 1-medical product 2-adverse event combination. The EBGM value is the geometric mean of a posterior distribution. The 5th (EB05) and 95th percentiles (EB95) of a posterior distribution create a two-sided 90% credibility interval.

Once the provider computing system 104 has determined one or more statistical values based on the selected case data, the method 300 proceeds to step 316 at which the provider computing system 104 determines one or more potential signals based on the one or more statistical values and the one or more statistical value minimums. As described herein, for each group of case data (e.g., for each MedDRA PT), the provider computing system 104 may determine whether the statistical values indicate the medical product and adverse event are a potential signal. For example, the provider computing system 104 may compare the statistical values with the minimum statistical values, and assuming they are greater than or equal to each of the respective minimums, determine the adverse event and medical product pair are a potential signal. If the statistical values are less than the minimum statistical values, the provider computing system 104 may determine the adverse event and medical product pair are not a potential signal. If the request identified an adverse event, the provider computing system 104 may compare the statistical values with the minimum statistical values, and assuming they are greater than or equal to each of the respective minimums, determine the adverse event and medical product pair are a potential signal.

In some embodiments, the provider computing system 104 may determine a potential signal in response to a single statistical value being greater than the corresponding minimum statistical value. In other embodiments, the provider computing system 104 may determine a potential signal in response to two or more statistical values being greater than the corresponding minimum statistical values. In some embodiments, the user via the user computing device 108 may set the number of statistical values that must be greater than the corresponding minimum statistical values to determine a potential signal (which may then be provided to the provider computing system 104). In other embodiments, the user via the user computing device 108 may set a specific set of one or more statistical values (e.g., PRR and case count, EBGM and PRR, etc.) that must be greater than the corresponding minimum statistical values to determine a potential signal (which may then be provided to the provider computing system 104).

Once the provider computing system 104 has determined one or more potential signals based on the one or more statistical values and the one or more statistical value minimums, the method 300 proceeds to step 320 at which the provider computing system 104 outputs the case data, the one or more statistical values, and/or the one or more potential signals. In some embodiments, the provider computing system 104 outputs the case data, the one or more statistical values, and/or the one or more potential signals to the user computing device 108. In some embodiments, the provider computing system 104 outputs each to the user computing device 108 enable display on a user interface as will be described further herein with regard to FIGS. 5A-7B. In some embodiments, the provider computing system 104 outputs the case data, the one or more statistical values, and/or the one or more potential signals to one or more of the health agency computing systems 112.

In some embodiments, once the provider computing system 104 has output the case data, the one or more statistical values, and/or the one or more potential signals, the provider computing system 104 may generate an electronic document including one or more of: the case data, the one or more statistical values, and/or the one or more potential signals. In some embodiments, the electronic document may be an aggregate or periodic report such as a Periodic Safety Update Report (PSUR) or a Periodic Benefit-Risk Evaluation Report (PBRER). In other embodiments, the electronic document may be an E2B XML file including one or more of: the case data, the one or more statistical values, and/or the one or more potential signals. In some embodiments, the provider computing system 104 generates the electronic document in response to receiving a verification or validation of the one or more potential signals. In some embodiments, the provider computing system 104 may receive at least a portion of the electronic document from the user computing device 108 and modify the electronic document to include the one or more of: the case data, the one or more statistical values, and/or the one or more potential signal. In some embodiments, the electronic document is an Excel file, a Comma Separated Value (CSV) file, a PDF file, or an HTML file.

Once the provider computing system 104 has generated the electronic document, the provider computing system 104 may output the electronic document. In some embodiments, the provider computing system 104 may output the electronic document to at least one of the user computing device 108 or one or more of the health agency computing systems 112. In some embodiments, the provider computing system 104 may output the electronic document (e.g., as an E2B XML file) to one or more of the health agency computing systems 112 via an AS2 Gateway communication.

In some embodiments, once the provider computing system 104 has output the case data, the one or more statistical values, and/or the one or more potential signals to enable display on the user interface, the provider computing system 104 may receive a request to track a specific potential signal from the user computing device 108. In response, the provider computing system 104 may generate a tracked signal data object associated with the specific medical product and a specific adverse event and store the tracked signal data object in a tracked signal repository (not shown). In some embodiments, the provider computing system 104 may then use the tracked signal data object to store case data, statistical values, and user inputs associated with the specific tracked signal (e.g., comments, analysis, etc.). In this regard, the electronic document described herein may be populated with the data of the tracked signal data object for reporting the specific tracked signal.

Referring now to FIGS. 4-8, user interfaces shown and displayed to the user of the user computing device 108 during the methods 200 and/or 300 are shown, according to example embodiments. As described herein, the user interfaces of FIGS. 4-8 may be one or more of web interfaces generated by the provider computing system 104 and rendered by the user computing device 108 as part of a web application or graphical user interfaces downloaded and generated by the user computing device 108 as part of a software application (e.g., a mobile application, etc.). Further, the user interfaces shown on FIGS. 4-8 allow for communication between the user and the provider computing system 104 via the user computing device 108 (specifically via the I/O circuit 162). Through interaction with the various user interfaces, the user may provide user input, feedback, and other data requested by the provider computing system 104. In this regard, it should be understood that each interaction described herein by the user with the user interfaces of FIGS. 4-8 may be provided to the user computing device 108 and then transmitted to the provider computing system 104 and that each action described herein as occurring to the user and/or the user computing device 108 (e.g., navigating to a certain page, generating a popup, etc.) may be performed by the provider computing system 104.

Referring now to FIG. 4, a medical product or signal product profile page 400, which can be displayed on a display of the I/O circuit 162 of the one or more of the user computing devices 108, is shown. In general, the signal product profile page 400 provides the respective user computing device 108 with an interface to initially set, view, and manage the settings for signal detection for a specific medical product (e.g., drug X) and provide any changes to the medical product data to the provider computing system 104. For example, via the signal product profile page 400, the user may provide initial medical product data associated with a medical product to the user computing 108, which may provide the initial medical product data to the provider computing system 104 to store within the medical product repository 134. In another example, via the signal product profile page 400, the user of the user computing device 108 may alter the medical product data associated with the medical product, which may be provided by the user computing device 108 to the provider computing system 104 for storage in the medical product repository 134. In this regard, the provider computing system 104 may provide medical product data associated with the medical product to the respective user computing device 108 to enable display of the signal product profile page 400 on the display of the I/O circuit 162. As shown, the signal product profile page 400 includes a signal product profile details section 404, a generate signals button 406, a medical product(s) section 430, a substance(s) section 462, and an other identifier(s) section 456.

The signal product profile details section 404 provides the user of the respective user computing device 108 with an interface to set, manage, and determine the signal details associated with the medical product and includes a profile name field 406, an organization field 408, a primary data source field 410, multiple minimum statistical value minimum fields (e.g., a PRR minimum field 412, an $x^2$ minimum field 414, an EBGM minimum field 416, an EB05 minimum field 418, and a minimum case count field 420), an include generic products checkbox or field 422, an include characterization concomitant checkbox or field 424, and an include characterization interacting field 426. It should be understood that each of the fields 406-420 may be included in or a part of the medical product data or signal product profile data described herein (e.g., with regard to step 210 or step 306).

The profile name field 406 is a selectable and/or editable text field through which the user of the respective user computing device 108 can edit the name of the signal product profile associated with the signal and the medical product which may then be sent by the respective user computing device 108 to the provider computing system 104 for storage. Similarly, the organization field 408 is a selectable and/or editable text field through which the user of the respective user computing device 108 can edit the organization or customer (e.g., Pharma X, Contract Research Organization X, etc.) associated with the signal product profile and the signal which may then be sent by the respective user computing device 108 to the provider computing system 104 for storage. In some embodiments, the organization field 408 may determine the permissions the user computing device 108 has (e.g., which medical products or medical product data objects the user computing device 108 can receive case data and medical product data in association with).

Likewise, the primary data source field 410 is a selectable and/or editable text field through which the user of the respective user computing device 108 can edit the default data source associated with the signal product profile and signals thereof which may then be sent by the respective user computing device 108 to the provider computing system 104 for storage. In some embodiments, the primary data source field 410 may determine which data source is automatically selected (and included in the request for case data as described with reference to the methods 200 and 300) when the user computing device 108 navigates to the signal detection page 500, as will be described further herein.

The multiple threshold statistical value minimum fields are each selectable and/or editable text fields through which the user of the respective user computing device 108 can edit the threshold statistical value of each of the specific statistical values associated with the signal product profile and signals thereof which may then be sent by the respective user computing device 108 to the provider computing system 104 for storage. For example, via the multiple threshold statistical value minimum fields the user can initially set or edit the threshold PRR value, the threshold $x^2$ value, the threshold EBGM value, the threshold EB05 value, the threshold (or maximum) EB95 value, the minimum number of cases, and the like.

The generate signals button 406 is a selectable or clickable button that, when selected, may cause the user computing device 108 to generate a request for case data (e.g., as described with regard to the method 300) associated with the medical product and the medical product data of the signal product profile page 400. Additionally, when the generate signals button 406 is selected the provider computing system may navigate the user computing device 108 to the signal detection page 500, which will described further herein.

The medical product(s) section 430 provides the user of the respective user computing device 108 with an interface to set, manage, and determine the medical products (e.g., medical product data object(s) associated with the signal product profile and the medical product data of the signal product profile page 400. As shown the medical product(s) section 430 includes one or more medical product or medical product data object representations 434.

Each medical product representation 434 may represent a specific medical product and/or medical product data object that is associated with the signal product profile of the signal product profile page 400. In this regard, it should be understood that multiple medical products may be associated with a single signal product profile. For example, the signal product profile may be associated with DrugX (30 MG) and DrugX (50 MG), which are considered two separate medical products. As shown, each medical product representation 434 includes a name field 436, a medical product field 438, a medical product brand or generic name field 440, a medical product type field 442, a medical product abbreviation field 444, and a medical product organization 446. It should be understood that each of the fields 436-446 may be included in or a part of the medical product data described herein.

The medical product name field 436 is a selectable and/or editable text field through which the user of the respective user computing device 108 can edit the name of the medical product or medical product data objective profile associated with the medical product of the medical product representation 434 which may then be sent by the respective user computing device 108 to the provider computing system 104 for storage. Likewise, the medical product brand or generic name field 408 is a selectable and/or editable text field through which the user of the respective user computing device 108 can edit or set the brand or generic name associated with the medical product of the medical product representation 434 which may then be sent by the respective user computing device 108 to the provider computing system 104 for storage.

Similarly, the medical product type field 442 is a selectable and/or editable text field or drop-down box with options through which the user of the respective user computing device 108 can edit and set the type of the medical product (e.g., Drug, Vitamin, Dietary Supplement, Medical Device, etc.) associated with the medical product representation 434 which may then be sent by the respective user computing device 108 to the provider computing system 104 for storage. Further, the medical product organization field 446 is a selectable and/or editable text field through which the user of the respective user computing device 108 can edit the organization or customer (e.g., Pharma X, Contract Research Organization X, etc.) associated with the medical product of the medical product representation 434 may then be sent to the provider computing system 104 for storage by the respective user computing device 108.

The substance(s) section 452 provides the user of the respective user computing device 108 with an interface to set, manage, and determine the substance(s) associated with the signal product profile and the medical product data of the signal product profile page 400. While not shown in detail, the substance(s) section 452 may include one or more substance representations (not shown). Each substance representation may represent a specific substance that is associated with the signal product profile of the signal product profile page 400. Each substance representation may include multiple substance fields which are editable. For example, each substance representation may include a substance name field, chemical formula field, a UNII field, and the like.

The other identifiers section 456 provides the user of the respective user computing device 108 with an interface to set, manage, and determine other medical product identifiers (i.e., outside of those included in the details section 404, the medical products section 430, and the substance(s) section 452) associated with the signal product profile and the medical product data of the signal product profile page 400. As shown, the other identifiers section 456 includes one or more medical product identifier representations 458.

Each medical product identifier representation 434 may represent a specific medical product identifier that is associated with the signal product profile and/or the medical product(s) of the signal product profile page 400. As shown, each medical product identifier representation 458 includes a medical product identifier name field 460, a medical product identifier value field 462, and a medical product identifier type field 464. It should be understood that each of the fields 460-464 may be included in or a part of the medical product data and/or the medical product identifiers described herein.

The medical product identifier type field 464 is a selectable and/or editable text field and/or drop-down box with options through which the user of the respective user computing device 108 can edit the type (e.g., Application Number, NDC-Product, NDC-Package, etc.) of the medical product identifier associated with the medical product identifier representation 458 which may then be sent by the respective user computing device 108 to the provider computing system 104 for storage. Likewise, the medical product identifier value field 462 is a selectable and/or editable text field through which the user of the respective user computing device 108 can edit or set the value of the medical product identifier associated with the medical product identifier representation 458 which may then be sent by the respective user computing device 108 to the provider computing system 104 for storage Referring now to FIGS. 5A-5B, a signal detection page 500, which can be displayed on a display of the I/O circuit 162 of one or more of the user computing devices 108, is shown. In general, the signal product profile page 400 provides one or more of the user computing devices 108 with an interface to view and manage case data, statistical values, and potential signals associated with a specific medical product or signal product profile (e.g., the medical product or signal product profile of the signal product profile page 400). In this regard, the signal detection page 500 may be associated with a specific medical product or signal product profile. To be navigated to the signal detection page 500, the user of the user computing device 108 may select the generate signals button 406 of the signal product profile page 400. In response to doing so, the user computing device 108 may generate a request for case data based on and including/identifying the medical product of the signal product profile page 400, as described with reference to the method 300. In this regard and in response, the provider computing system 104 may provide the resulting case data, statistical values, and potential signals to the respective user computing device 108 to enable display of the signal detection page 500 on the display of the I/O circuit 162. As shown, the signal detection page 500 includes a refresh button 502, an options section 504, a statistical value chart or graph 522, a heat map 530, and a list of detected or potential signals 540.

The refresh button 502 is a selectable or clickable button that, when selected, may cause the user computing device 108 to generate a request for case data and provide the request to the provider computing system 104. In this regard, by selecting the refresh button 502, the user computing device 108 receives the newest updated case data, statistical values, and potential signals from the provider computing system 104 in real-time. In some embodiments, the user computing device 108 may generate the request to identify or include the data sources, the timeframe, and the filters of the options section 504.

Through refreshing the case data with a selection of the refresh button 502 (and/or the apply button 518) by receiving a new request for case data and then outputting updated case data, the provider computing system 104 and the system 100 provide for an improved signal detection system. Typically, signal detection systems require manual labor-intensive queries to be setup by a user and then run over a long set of time (e.g., overnight, over the weekend, etc.)

before new case data is received and ready for analysis. In this regard, the system 100 provides for a quicker, real-time, process and system for receiving updated case data through the use of the request for case data. For instance, by utilizing a simple request, and not a manual labor-intensive query, the system 100 simplifies the process for request and receiving refreshed/updated case data, and thereby uses less processing power and memory. For instance, instead of taking a long set of time to return updated case data, the system 100 utilizes the request which saves on processing power and memory and returns refreshed case data within a matter of minutes.

The options section 504 provides the user of the respective user computing device 108 with an interface to set, manage, and determine the filters, electronic data sources, and the timeframe which are applied to the case data received from the provider computing system 104 and received and displayed on the signal detection page 500. As shown the options section 504 includes multiple electronic data source checkboxes (e.g., the FAERs checkbox 506 and the trusted or PV case repository checkbox 507), one or more timeframe or reporting period fields 508, multiple filter fields (e.g., the PRR minimum field 510, the $x^2$ minimum field 512, the EBGM minimum field 514, the EB05 minimum field 516), and an apply button 518. In some embodiments, the multiple electronic data source checkboxes and multiple filter fields may be prepopulated with values based on the medical product or signal product profile of the signal product profile page 400. For instance, the multiple electronic data source checkboxes may be checked or unchecked based on the primary data source field 410 of the medical product field. For example, the FAERs checkbox 506 may be selected or checked and the trusted or PV case repository checkbox 507 may be unselected or not checked, in response to the primary data source field 410 identifying FAERS as the primary data source. In another example, the PRR minimum field 510 may be prepopulated with the PRR minimum value of the PRR minimum field 412 of the signal product profile page 400. In some embodiments, the prepopulates values may then be used to generate the request for case data (e.g., included in the request for case data).

The multiple electronic data source checkboxes or fields are each a selectable and editable checkbox through which the user of the respective user computing device 108 can set the one or more electronic data sources to be included in the request for case data described herein. For instance, by selecting the FAERs checkbox 506 and the trusted or PV case repository checkbox 507, the user computing device 108 may include or identify each within the request for case data (as described with regard to the step 228 of the method 200). Likewise, the multiple filter fields are each selectable and editable text fields through which the user of the respective user computing device 108 can set the filters to be included in the request for case data described herein.

Figure 5A:
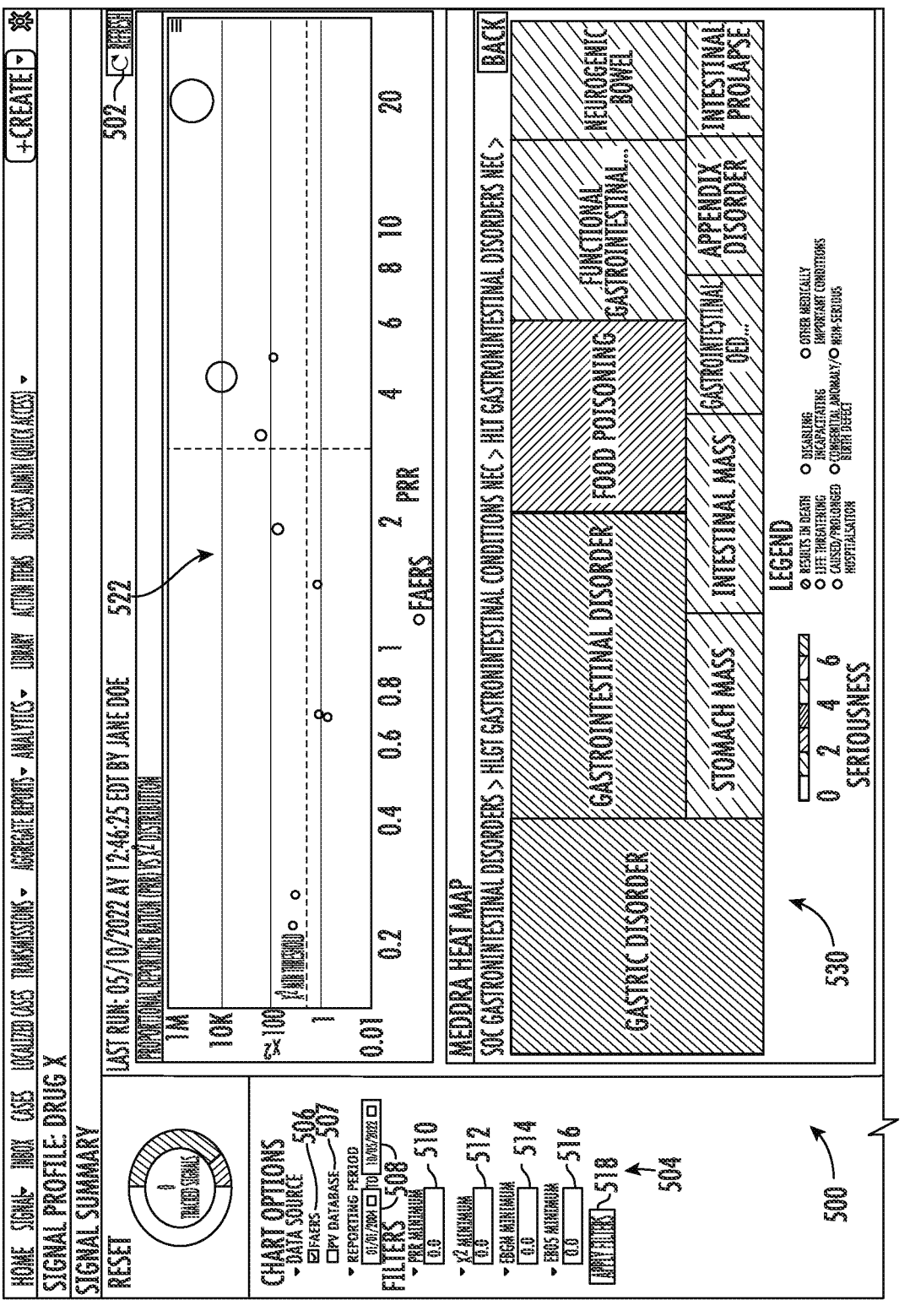
FIGS. 5A-5B are illustrations of some aspects of a user interface generated by the standardized case dataset collection and signal detection system of FIG. 1 to manage determined potential signals, according to an example embodiment.
Figure 5B:
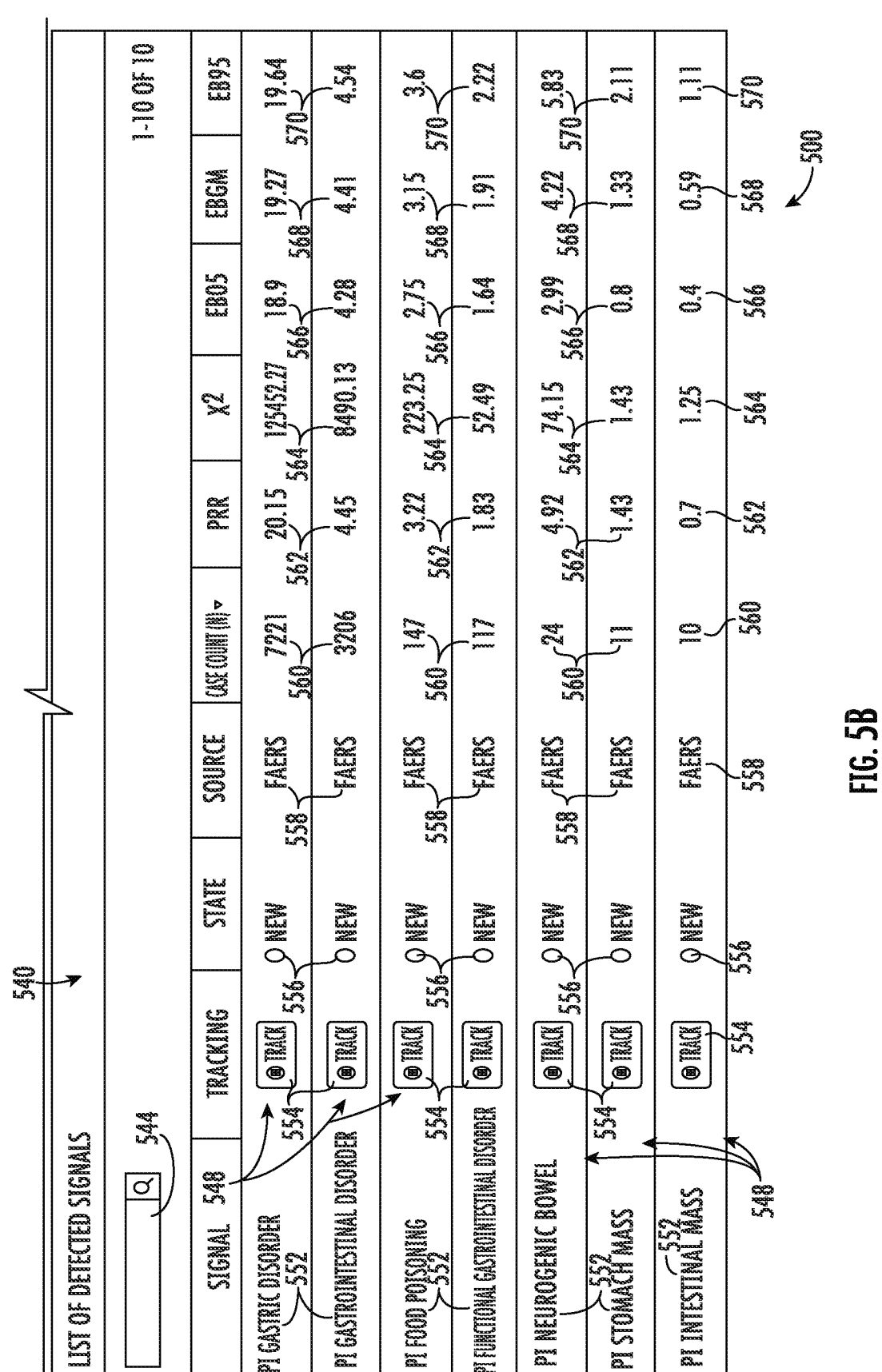

The timeframe fields 508 are selectable and editable date/time fields through which the user of the of the respective user computing device 108 can set the timeframe (e.g., the active start date and the active end date) to be included in the request for case data described herein. For instance, via the timeframe fields 508, the user of the user computing device 108 may set the active start date to be Jan. 1, 2004 and the active end date to be Oct. 5, 2022 (as shown in FIG. 5A).

In some embodiments, the apply or apply filters button 518 is a selectable button that, when selected, may cause the user computing device 108 to filter the received case data and generate the statistical value chart or graph 522, the heat map 530, and the list of detected or potential signals 540 using the filtered case data. In other embodiments, when the apply button 518 is selected, the user computing device 108 may generate a request for case data including or identifying the data source, the timeframe, and the filters of the fields of the options section 504 (e.g., similar to or the same as the refresh button 502). In response, the provider computing system 104 may provide updated case data, statistical values, and potential signals to the user computing device 108 to enable display on the signal detection page 500 of the statistical value chart or graph 522, the heat map 530, and the list of detected or potential signals 540 including the updated data, values, and signals.

The statistical value chart or graph 522 is a graph or chart that displays the received one or more statistical values in comparison. For example, as shown, the statistical value graph 522 is a bubble chart that includes PRR on the Y-axis and $x^2$ on the X-Axis. In some embodiments, the user of the user computing device 108 may select which statistical value is to be displayed on the X-Axis and which statistical value is to be displayed on the Y-Axis. In this regard, each of the bubbles shown may be a group of case data which is grouped by adverse event term (e.g., MedDRA PT), as described herein with regard to the method 300. Larger circles or bubbles may indicate a larger number of cases, as compared to smaller circles or bubbles. In some embodiments, the bubbles may be colored to provide an indication of the electronic data source from which they came (e.g., blue indicates FAERS, Yellow indicates the trusted or PV case repository 146, red indicates both, etc.). In some embodiments, the statistical graph 522 is interactive such that the user can select or zoom in/out on the data included in the graph 522 to change the amount of data appearing on the graph 522.

In some embodiments, if the user selects or clicks on one of the bubbles of the graph, the heatmap 522 and the list of detected or potential signals 540 may display data associated with that bubble (e.g., with the group of cases associated with that bubble). In this regard, selecting case data within the statistical value chart or graph 522, the heat map 530, and/or the list of detected or potential signals 540 may cause the user computing device 108 or the provider computing system 104 to filter the case data of the signal detection page 500 to the selected data.

The MedDRA heatmap 530 is a graph or chart that displays the received case data in a heatmap based on the seriousness, the MedDRA terms used to group the case data, and volume (e.g., number of cases) of the case data. Further, the heatmap 530 may be interactive and display the case data based on the MedDRA hierarchy. For example, when the user first navigates to the signal detection page 500, the heatmap 530 may display the applicable SOC terms (e.g., highest level terms) of the MedDRA hierarchy (e.g., SOC terms which match cases of the received case data) within a tile of the heatmap. The tile including the SOC terms may be colored based on the seriousness of the (majority of) cases therein (e.g., red for serious results in death, blue for serious "other medically important conditions, white for non-serious, etc.) and sized based on the volume of the cases therein (e.g., proportionally to one another). For instance, a tile including a SOC (e.g., Gastrointestinal disorders) that is associated with two cases that both resulted in death may be colored in red and twice the size of a tile that is associated with a single case.

Additionally, the user of the user computing device 108 may then be able to select the tile to see the next hierarchy of classes. For instance, the tile including the SOC Gastrointestinal disorders may be selected to display tiles of the next class (e.g., HLGT) that are applicable to the received cases (e.g., Diverticular disorders, Gastrointestinal infections, Gastrointestinal vascular conditions, etc.). This process may be repeated until reaching the lowest level of terms within the MedDRA hierarchy. In some embodiments, the user computing device 108 may automatically navigate the heatmap 530 to the MedDRA hierarchy level associated with a MedDRA term selected on the graph 522.

The list of detected or potential signals 540 is an interactive list of the determined potential signals (as discussed with regard to step 312) through which the user of the user computing device 108 can interact to manage and process the potential signals. As shown, the list of potential signals 540 includes a search bar or field 544 and multiple potential signal representations 548. The search bar or field 544 is a selectable text field through which the user of the user computing device 108 can filter the multiple potential signal representations 548 that are shown within the list of potential signals 540. For example, the user may enter the term "Gastric Disorder" into the search field 544, and the user computing device 108 may filter the displayed potential signal representations 548 down to a single potential signal representation 548 associated with the adverse event Gastric Disorder. In some embodiments, the user computing device 108 may automatically display the potential signal representations 548 associated with a MedDRA term selected on the graph 522.

Each potential signal representation 548 may represent a specific determined potential signal that is associated with the medical product and adverse event groups of the signal detection page 500. As shown, each potential signal representation 548 includes a signal or adverse event field 552, a tracking button 554, a state field 556, a source field 558, and multiple statistical value fields (e.g., a case count field 558, a PRR field 560, an $x^2$ field 562, an EB05 field 564, an EBGM field 568, and an EB95 field 570).

The signal or adverse event field 552 may be a text field that indicates and displays the adverse event term (e.g., MedDRA PT) of the potential signal associated with the potential signal representation 548. Similarly, the state field 556 and the data source field 556 may each be text fields that indicate and display the state (e.g., new, tracked, validated, verified, submitted, etc.) and the electronic data source, respectfully, of the potential signal associated with the potential signal representation 548.

The tracking button 554 is a selectable button that, when selected, may navigate the user computing device 108 to a signal page 600 through which the user of the user computing device 108 can assess and/or submit (e.g., within an electronic document) the potential signal associated with the potential signal representation 548. In some embodiments, the tracking button 554, when selected, may cause the user computing device 108 to provide an indication of such to the provider computing system 104. In response, the provider computing system 104 may generate one or more alerts or other notifications when changes occur to the signal (e.g., when new case data associated with the potential signal is received, when the statistical values associated with the signal change, etc.).

The multiple statistical value fields may each be text fields that indicate and display the statistical values of the potential signal associated with the potential signal representation 548. For instance, the potential signal representation may include a PRR field 560 that displays the PRR value associated with the potential signal of the potential signal representation 548. In some embodiments, statistical values which are below the respective minimum statistical values may be indicated as such on the potential signal representation 548. For instance, the statistical value fields which are below the minimum statistical values may be highlighted, emphasized, colored, or otherwise indicated (e.g., include an asterisk) as such.

While not shown, the signal detection page 500 may further include a case listing or case listing section. The case listing may be an interactive list of the received cases associated with the medical product and/or the potential signals. The case listing may include a search bar or field, a data source field, an adverse event field, a seriousness field, a date/time field (e.g., date of receipt, date of new info), and/or a version field.

Figure 6:
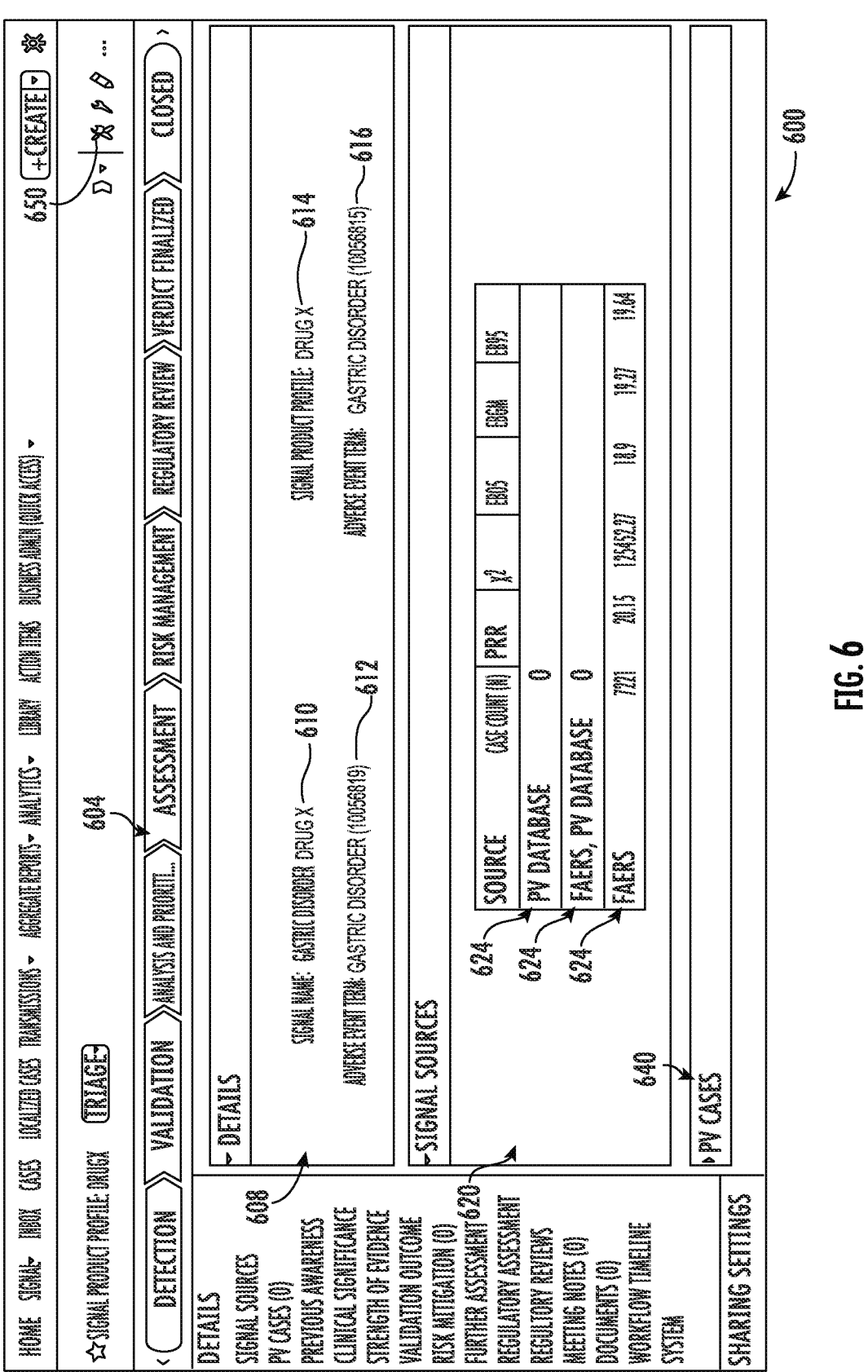
FIG. 6 is an illustration of some aspects of a user interface generated by the standardized case dataset collection and signal detection system of FIG. 1 to monitor a specific potential signal, according to an example embodiment.

Referring now to FIG. 6, a signal page 600, which can be displayed on a display of the I/O circuit 162 of one or more of the user computing devices 108, is shown. In general, the signal page 600 provides one or more of the user computing devices 108 with an interface to view and manage a specific potential signal. In this regard, the signal page 600 may be associated with a specific medical product or signal product profile and adverse event. To be navigated to the signal page 600, the user of the user computing device 108 may select the track signal button 554 of the signal detection page 500. In response to doing so, the user computing device 108 may generate a request for case data based on and identifying the medical product and adverse event associated with the signal page 600, as described with reference to the method 300. In this regard and in response, the provider computing system 104 may provide the resulting case data and statistical values to the respective user computing device 108 to enable display of the signal page 600 on the display of the I/O circuit 162. In some embodiments, the provider computing system 104 may generate a signal data object, in response to the user selecting the track signal button 554 of the signal detection page 500, and the signal data object may include the resulting case data and statistical values. As shown, the signal page 600 includes a state section 604, a signal details section 608, a signal sources section 620, a case listing section 640, and a workbench button 650.

The state section 604 provides the user of the user computing device 108 with an indication of the state that the signal associated with the signal page 600 is currently in. In some embodiments, the user of the user computing device 108 may provide an indication of verification and validation via the state section 604. In this regard, the signal of the signal page 600 may progress through the various states of the state section 604 until reaching a closed state (e.g., submitted, closed, etc.). It should be understood that states outside of those shown in the state section 604 are possible (e.g., submitted).

The signal details section 608 provides the user of the user computing device 108 with an indication of high-level details regarding the signal associated with the signal page 600. As shown, the signal details section 608 includes a signal name field 610, a first adverse event term field 612, a second adverse event term field 616, and a signal product profile field 614.

The signal name field 610 may be a selectable and/or editable text field through which the user of the respective user computing device 108 can edit the name of the signal associated with the signal page 600 which may then be sent by the respective user computing device 108 to the provider computing system 104 for storage. Similarly, the signal product profile field 614 may be a selectable and/or editable text field or drop-down box with options through which the user of the respective user computing device 108 can edit and set the signal product profile associated with the signal of the signal page 600 which may then be sent by the respective user computing device 108 to the provider computing system 104 for storage. In some embodiments, the signal product profile is the signal product profile or medical product associated with the signal detection page 500 that was used to navigate to the signal page 600.

The first adverse event term field 612 and the second adverse event term field 616 are each editable text fields or drop-down box with options through which the user of the respective user computing device 108 can edit and set a first adverse event and/or second adverse event associated with the signal of the signal page 600 which may then be sent by the respective user computing device 108 to the provider computing system 104 for storage. As described herein, signals may look at results between a medical product-adverse event pair or a medical product 1-medical product 2-adverse event pair. In this regard, the details section 608 may include the first adverse event term field 612 and the second adverse event term field 616. In signals which are only looking at a medical product-adverse event pair, the second adverse event term field 616 may be the same as the first adverse event term field 612 (as shown in FIG. 6).

The signal sources section 620 provides the user of the user computing device 108 with a breakdown, by electronic data source, of the received case data and statistical values associated of the signal associated with the signal page 600. As shown, the signal sources section 620 includes a signal sources table with multiple signal source rows or portions 624.

The signal source rows or portions 624 each represent an electronic data source and include/display multiple statistical values associated with the case data of the respective data source. For example, the signal sources section 620 includes a first signal source portion 624 associated with the PV or trusted case repository 146 (as discussed with regard to the step 236 of the method 200), a second signal source portion 624 associated with the health agency case repository 184 (e.g., FAERS) and the PV repository in conjunction (e.g., as discussed with regard to the step 240 of the method 200), and a third signal source portion 624 associated with the health agency case repository 184 (e.g., FAERS) (as discussed with regard to the step 238 of the method 200). Further, each signal source portion 624 includes a case count field, a PRR field, an $x^2$ field, an EB05 field, an EBGM field, and an EB95 field.

By breaking down the case data and statistical values by each electronic data source, the signal page 600 provides for additional insights that are not available in typical signal detection systems. For instance, by breaking the case counts down by source (e.g., 10 cases from FAERS, 10 cases from the trusted case repository 146, 15 cases from FAERS and the trusted case repository 146 combined), the user computing device 108 (and the provider computing system 104) are able to distinguish trends that are not available in typical signal detection systems. For instance, because cases that have been provided to FAERS should have been reported by the PV circuit 144, the user computing device 108 (and the provider computing system 104) can analyze the source specific case counts to determine cases that were not reported by the PV circuit 144 to FAERS. In some embodiments, the provider computing system 104 may automatically analyze which cases have not been received or processed by the PV circuit 144 and provide an indication to the user computing device 108 of the specific cases. In another example, the user computing device 108 (and the provider computing system 104) can analyze which sources contain the most unique cases (e.g., cases with no matches in the other case repositories) and the least unique cases to better determine the priority of the electronic data sources based on the source specific case counts.

While not shown in detail, the case listing section 640 may be an interactive list of the received cases associated with the signal of the signal page 600. The case listing section 640 may include a search bar or field, a data source field, an adverse event field, a seriousness field, a date/time field (e.g., date of receipt, date of new info), and/or a version field.

The tracking button 554 is a selectable button that, when selected, may navigate the user computing device 108 to a signal page 600 through which the user of the user computing device 108 can assess and/or submit (e.g., within an electronic document) the potential signal associated with the potential signal representation 548. In some embodiments, the tracking button 554, when selected, may cause the user computing device 108 to provide an indication of such to the provider computing system 104. In response, the provider computing system 104 may generate one or more alerts or other notifications when changes occur to the signal (e.g., when new case data associated with the potential signal is received, when the statistical values associated with the signal change, etc.).

The workbench button 650 is a selectable button that, when selected, may navigate the user computing device 108 to a workbench page 700 through which the user of the user computing device 108 can assess and more finely analyze the signal of the signal page 600. In some embodiments, the user computing device 108 or the provider computing system 104 may use the received case data of the signal page 600 when generating and navigating to the workbench page 700.

Figure 7B:
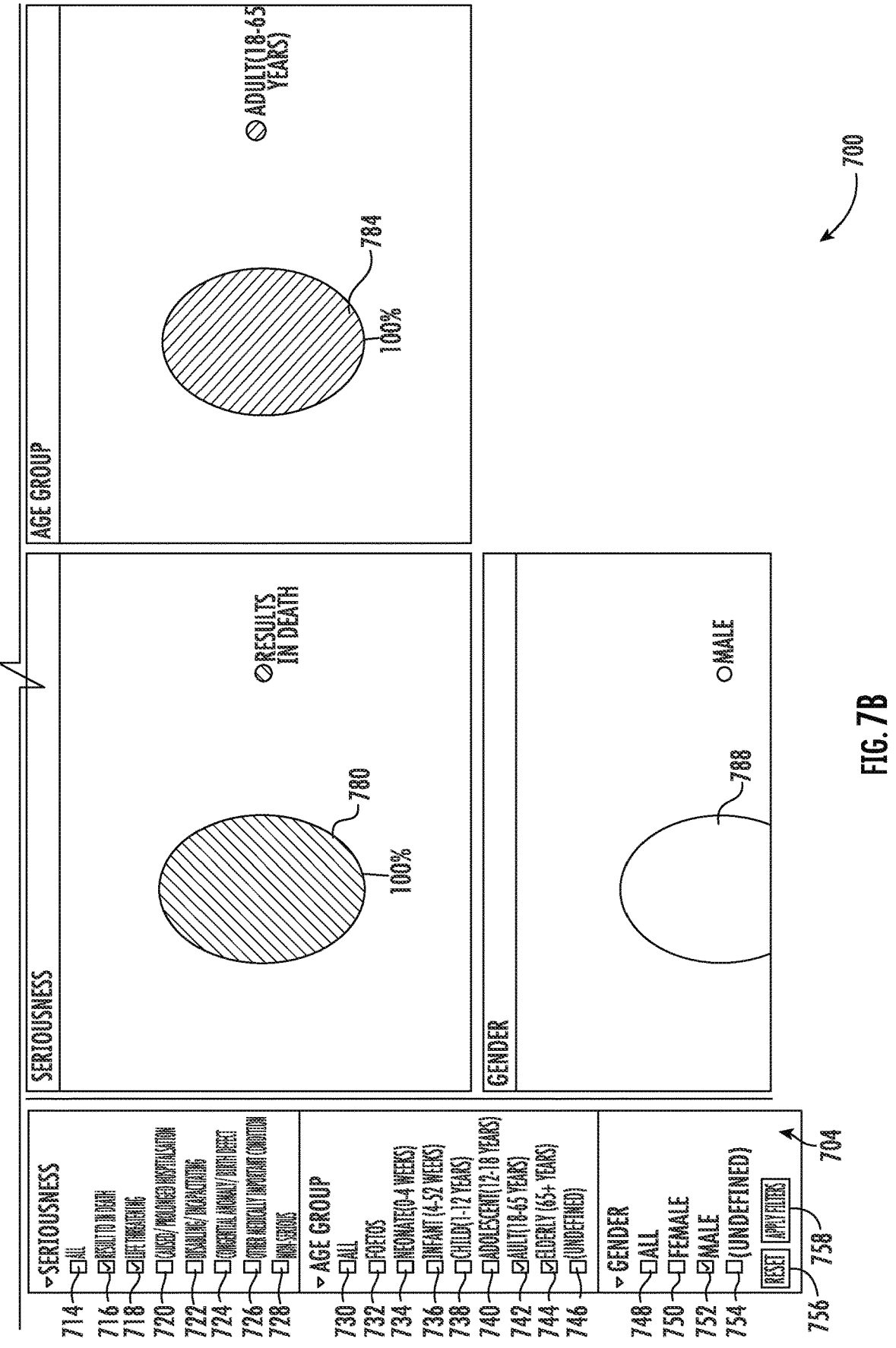

Referring now to FIGS. 7A-7B, the workbench page 700, which can be displayed on a display of the I/O circuit 162 of one or more of the user computing devices 108, is shown. In general, the workbench page 700 provides one or more of the user computing devices 108 with an interface to view and analyze the signal of the signal page 600. To be navigated to the workbench page 700, the user of the user computing device 108 may select the workbench button 650 of the signal page 600. In response to doing so, the user computing device 108 may generate a request for case data based on and identifying the medical product and adverse event associated with the signal of the signal page 600, as described with reference to the method 300. In this regard and in response, the provider computing system 104 may provide the resulting case data and statistical values to the respective user computing device 108 to enable display of the workbench page 700 on the display of the I/O circuit 162. In some embodiments, the user computing device 108 or the provider computing system 104 may use the received case data of the signal page 600 to enable display of the workbench page 700. As shown, the workbench page 700 includes a filters or options section 704, a signal source summary section 760, and a signal analytics section or dashboard 770.

The filters or options section 704 provides the user of the respective user computing device 108 with an interface to set, manage, and determine the filters, electronic data sources, and the timeframe which are applied to the case data received from the provider computing system 104 and received and displayed in the signal analytics section or dashboard 770. As shown the options section 704 includes multiple electronic data source checkboxes (e.g., the all sources checkbox 708, the FAERs checkbox 709, and the trusted or PV case repository checkbox 710), one or more timeframe or reporting period fields 712, multiple seriousness filter fields or checkboxes (e.g., the all seriousness's checkbox 714, the results in death seriousness checkbox 716, the life threatening seriousness checkbox 718, the caused/prolonged hospitalization seriousness checkbox 720, the disabling/incapacitating seriousness checkbox 722, the congenital anomaly/birth defect seriousness checkbox 724, the other medically important condition seriousness checkbox 726, and the non-serious checkbox 728), multiple age group filter fields or checkboxes (e.g., the all age group checkbox 730, the Fetus age group checkbox 732, the neonate age group checkbox 734, the infant age group checkbox 736, the child age group checkbox 748, the adolescent age group checkbox 740, the adult age group checkbox 742, the elderly age group checkbox 744, and the undefined age group checkbox 746), the multiple gender filter fields or checkboxes (e.g., the all genders checkbox 748, the female gender checkbox 750, the male gender checkbox 752, and the undefined gender checkbox 754), the reset button 756, and the apply filters button 758.

The multiple electronic data source checkboxes or fields are each a selectable and editable checkboxes through which the user of the respective user computing device 108 can set the one or more electronic data sources to be included in the request for case data described herein. For instance, by selecting the FAERs checkbox 709, the user computing device 108 may include or identify each within the request for case data (as described with regard to the step 228 of the method 200).

Likewise, the multiple filter fields (e.g., the multiple age group filter checkboxes, the multiple seriousness filter checkboxes, the multiple gender filter checkboxes, etc.) are each selectable and editable checkboxes through which the user of the respective user computing device 108 can set the filters to be included in the request for case data described herein. For instance, by selecting the Fetus age group checkbox 732, the neonate age group checkbox 734, and the all seriousness's checkbox 714, the user computing device 108 may include or identify the case data is to be for cases that are within the neonate age group, the fetus age group, and all seriousness types.

The timeframe fields 712 are selectable and editable date/time fields through which the user of the of the respective user computing device 108 can set the timeframe (e.g., the active start date and the active end date) to be included in the request for case data described herein. For instance, via the timeframe fields 712, the user of the user computing device 108 may set the active start date to be Jan. 1, 2004 and the active end date to be Oct. 5, 2022 (as shown in FIG. 7A).

In some embodiments, the apply or apply filters button 756 is a selectable button that, when selected, may cause the user computing device 108 to filter the received case data and generate the analytics dashboard 770 using the filtered case data. In other embodiments, when the apply filters button 756 is selected, the user computing device 108 may generate a request for case data including or identifying the data source, the timeframe, and the filters of the fields of the filters section 704. In response, the provider computing system 104 may provide updated case data, statistical values to the user computing device 108 to enable display on the workbench page 700 of the analytics dashboard 770.

The signal source summary section 760 provides the user with a summary of the signal associated with the workbench page 700 and analyzes the statistical values associated with the signal by electronic data source. As shown, the signal source summary section 760 includes a signal source graph or chart 762 and a signal sources table with multiple signal source rows or portions 764. In this regard, the analytics dashboard 770 provides an interface or dashboard to apply and view the case data with the one or more filters and the signal source summary section 760 represents the case data prior to the filters being applied.

The signal source rows or portions 764 each represent an electronic data source and include/display multiple statistical values associated with the case data of the respective data source. For example, the signal source summary section 760 includes a first signal source portion 764 associated with the PV or trusted case repository 146 (as discussed with regard to the step 236 of the method 200), a second signal source portion 764 associated with the health agency case repository 184 (e.g., FAERS) and the PV repository in conjunction (e.g., as discussed with regard to the step 240 of the method 200), and a third signal source portion 764 associated with the health agency case repository 184 (e.g., FAERS) (as discussed with regard to the step 238 of the method 200). Further, each signal source portion 764 includes a case count field, a PRR field, an $x^2$ field, an EB05 field, an EBGM field, and an EB95 field.

Similarly, the signal source graph or chart 762 is a chart that displays the one or more statistical values of each signal source portion 764 in comparison. For instance, in FIG. 7A, the signal source chart 762 is a pie chart that displays the case count of the first signal source portion 764, the second signal source portion 764, and the third signal source portion 764 in comparison with one another. In some embodiments, the signal source graph or chart 762 may be a different type of chart or graph (e.g., bar chart, bubble chart, etc.).

The analytics dashboard or section 770 provides the user with the filtered cases of the signal associated with the workbench page 700. As shown, the analytics dashboard or section 770 includes a filtered signal sources table with one or more filtered signal source rows or portions 772, a filtered seriousness chart or graph 780, a filtered age group chart or graph 784, and a filtered gender chart or graph 788.

The filtered signal source rows or portions 772 each represent an electronic data source and include/display multiple statistical values associated with the filtered case data of the respective data source based on the filters of the filter section 704. For example, the filtered signal sources table is shown to include a first filtered signal source portion 772 associated with the health agency case repository 184 (e.g., FAERS). Similar to the signal source portion 764, each filtered signal source portion 772 includes a case count field, a PRR field, an $x^2$ field, an EB05 field, an EBGM field, and an EB95 field.

The filtered seriousness chart or graph 780 is a chart that displays the one or more statistical values of the filtered case data in comparison based on seriousness. For instance, in FIG. 7B, the filtered seriousness chart 780 is a pie chart that displays the case count (or a percentage of the whole thereof) of the filtered cases based on seriousness (e.g., 25% of the cases are serious: results in death, 25% of the cases are serious: life threatening, and so on). In some embodiments, the filtered seriousness chart or graph 780 may be a different type of chart or graph (e.g., bar chart, bubble chart, etc.).

Likewise, the filtered age group chart or graph 784 is a chart that displays the one or more statistical values of the filtered case data in comparison based on age group. For instance, in FIG. 7B, the filtered age group chart 784 is a pie chart that displays the case count (or a percentage of the whole thereof) of the filtered cases based on age group (e.g., 25% of the cases are within the neonatal age group, 25% of the cases are in the adult age group, and so on). In some embodiments, the filtered age group chart 784 may be a different type of chart or graph (e.g., bar chart, bubble chart, etc.).

The filtered gender chart or graph 788 is a chart that displays the one or more statistical values of the filtered case data in comparison based on gender. For instance, in FIG. 7B, the filtered gender chart 788 is a pie chart that displays the case count (or a percentage of the whole thereof) of the filtered cases based on gender (e.g., 50% of the cases are males and 50% of the cases are females). In some embodiments, the filtered gender chart 788 may be a different type of chart or graph (e.g., bar chart, bubble chart, etc.).

Figure 8:
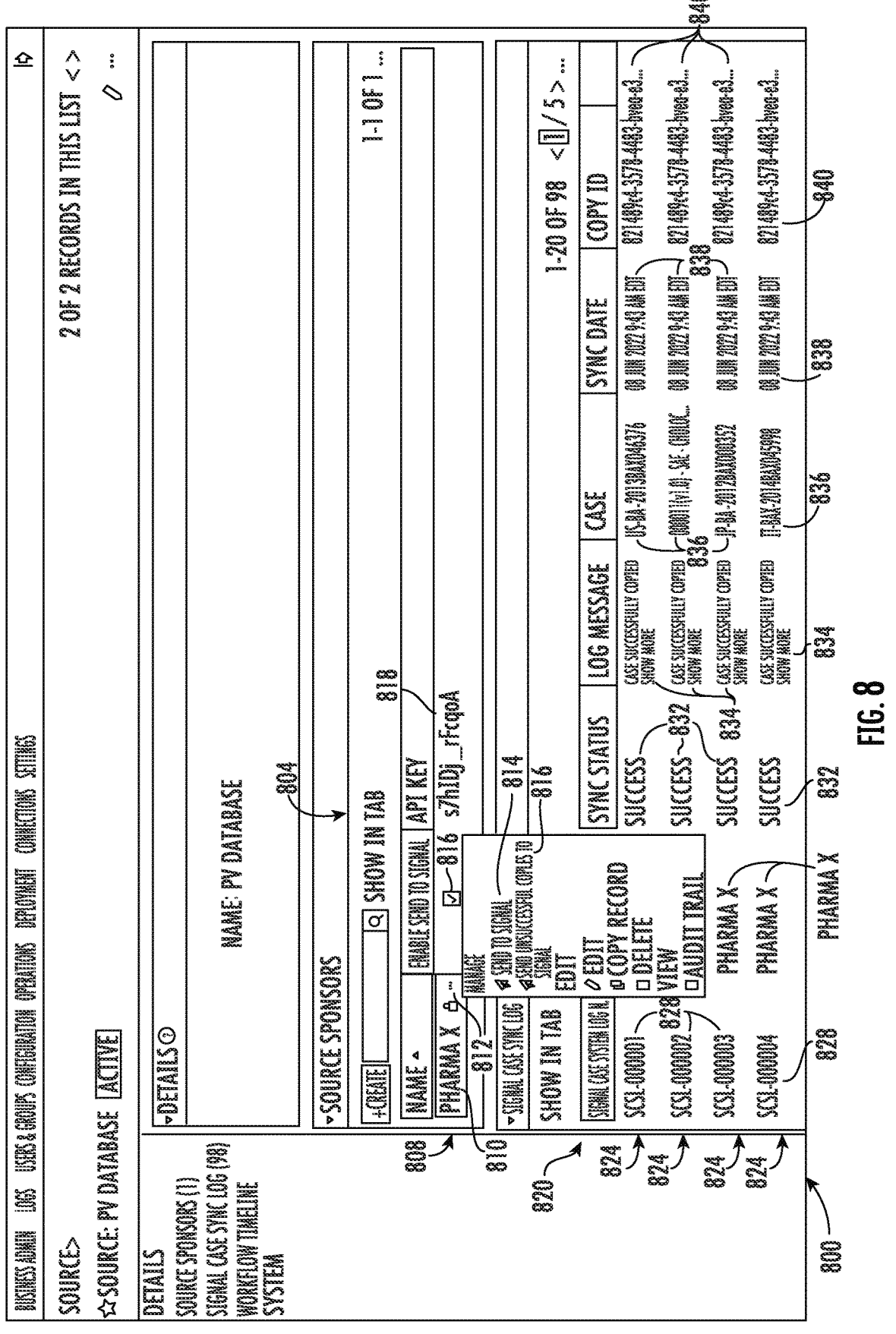
FIG. 8 is an illustration of some aspects of a user interface through which the standardized case dataset collection and signal detection system of FIG. 1 receives a request to copy trusted case data from a trusted case repository to a central case data warehouse, according to an example embodiment.

Referring now to FIG. 8, the PV repository management page 800, which can be displayed on a display of the I/O circuit 162 of one or more of the user computing devices 108, is shown. In general, the PV repository management page 800 provides one or more of the user computing devices 108 with an interface to view, manage, and request the transfer of the trusted case data of the trusted case repository 146 to the central case data warehouse 130 (e.g., to the one or more PV repositories 132). In this regard, the provider computing system 104 may provide the medical product data associated with the customer to the user computing device 108 to enable display PV repository management page 800. As shown, the PV repository management page 800 includes a trusted case data management section 804 and a case sync log section 820.

The trusted case data management section 804 provides the user of the respective user computing device 108 with an interface to manage the transfer of the trusted case data from the trusted case repository 146 to the central case data warehouse 130. As shown the trusted case data management section 804 includes a PV repository representation 808.

Each PV repository representation 808 may represent a specific central PV case repository 132 and/or the medical product or customer with which the PV repository is associated. As shown, each PV repository representation 808 includes a name field 810, an options button 812, an enable send to signal checkbox 816, and an API key field 818.

The name field 810 is a selectable and/or editable text field through which the user of the respective user computing device 108 can edit the name of the PV repository associated with the PV repository representation 808 which may then be sent by the respective user computing device 108 to the provider computing system 104 for storage.

The options button 812 is a selectable button that, when selected, drops down multiple options including a send to signal option 814 and a send unsuccessful copies to signal option 816. The send to signal (also referred to as send to central case data warehouse) option 814 is a selectable option that, when selected, provides a request to the provider computing system 104 to copy all of the cases associated with the medical product or customer associated with the PV repository and the related trusted case data within the trusted case repository 146 to the central case data warehouse 130. In this regard, in response to receiving the request, the provider computing system 104 (e.g., the PV circuit 144) may select each of the resulting cases and related trusted case data from the trusted case repository 146 and provide a copy of each to the central case data warehouse 130 for storage in one of the central PV case repositories 132. In some embodiments, the send to signal option 814 provides a request to the provider computing system 104 to copy all of the cases within one or more certain states (e.g., closed, superseded, voided, nullified, etc.) and associated with the medical product or customer associated with the PV repository and the related trusted case data within the trusted case repository 146 to the central case data warehouse 130.

Similarly, the send unsuccessful copies to signal (also referred to as send to central case data warehouse) option 816 is a selectable option that, when selected, provides a request to the provider computing system 104 to copy all of the cases that previously failed to copy (as indicated in the case sync log section 820). In this regard, in response to receiving the request, the provider computing system 104 (e.g., the PV circuit 144) may select each of the resulting cases and related trusted case data from the trusted case repository 146 and provide a copy of each to the central case data warehouse 130 for storage in one of the central PV case repositories 132.

The enable send to signal checkbox 816 is a selectable checkbox that, when checked, provides an indication that cases of the trusted case repository 146 are to be automatically copied to the central case data warehouse 130, when moved to a closed state. In this regard, when the user checks the enable send to signal checkbox 816, the user computing device 108 may send an indication of such. Then, when a case of the PV circuit 144 moves to a closed state, the provider computing system 104 (e.g., the PV circuit 144) may send the closed case and related trusted case data from the trusted case repository 146 and provide a copy to the central case data warehouse 130 for storage in one of the central PV case repositories 132.

The API key 818 is a text field that indicates or includes an application programming interface (API) key associated with the central PV case repository 132 of the central case data warehouse 130 to which the trusted case data is provided.

The case sync log section 820 provides the user of the respective user computing device 108 with an interface to manage and view the status of cases that were transferred from the trusted case repository 146 to the central case data warehouse 130. As shown the case sync log section 820 includes multiple case transmission representations 824.

Each case transmission representation 824 may represent a specific attempt at copying a case from the trusted case repository 146 to the central case data warehouse 130. As shown, each case transmission representation 824 includes a name field 828, an associated customer field 830, a sync status field 832, a log message 834, an associated case field 836, a sync date/time field 838, and a copy ID field 840. In some embodiments, the transmission representation 824 may further include a medical product field (not shown)

The name field 828 is a text field that includes the name of the case transmission associated with the case transmission representation 824. Similarly, the associated customer field 830 is a text field that includes the customer with which the case is associated.

The sync status field 832 is a text field that includes the status of the case transmission associated with the case transmission representation 824. For example, the sync status field 832 may include the status "Success", "Failure", "Pending", "Paused", and the like. In this regard, the send unsuccessful copies to signal option 816 may apply to case transmissions with the status "Failure".

The log message 834 is a text field that includes a system (e.g., the provider computing system 104) generated message associated with the sync status of the sync status field 832. For instance, when a case transmission was successful the log message 834 may include the system generated message "Case successfully copied". In other example, the log message 834 may include a message explaining a case transmission with the status "Failure" (e.g., "Case could not copy due to case missing a narrative" "Case could not copy due to the case being reopened", etc.).

The associated case field 836 is a selectable text field that includes the case associated with the case transmission representation 824. In some embodiments, the associated case field 836 is a selectable link that, when selected, navigates the user of the user computing device 108 to a case page (not shown) associated with the specific case.

The sync date/time field 838 is a date/time field that includes the date/time the case transmission attempted to process, failed to process, successfully processed, and the like. Similarly, the copy ID field 840 is a text field that includes a unique ID associated with the transmission of the case such that the transmission can be identified.

Referring now to FIGS. 9A-9C, multiple example embodiments of the central case data warehouse 130 are shown. FIG. 9A shows a central case data warehouse 130A including multiple health agency repositories (also referred to as central health agency case repositories) 131, multiple PV repositories (also referred to as central PV case repositories) 132, and multiple additional case repositories (also referred to as central additional case repositories) 133. As described herein, the central case data warehouse 130A may include a central health agency case repository 131 for each of the health agency computing systems 112 from which health agency case data is received. For instance, central case data warehouse 130A may include a first central health agency case repository 131 in which combined health agency case data associated with and received from the FDA (e.g., FAERS) is stored and a second central health agency case repository 131 in which combined health agency case data associated with and received from Health Canada is stored. In this regard, the central case data warehouse 130A (or the health agency repository 131), when requested or queried, may output the combined health agency case data of the respective central health agency case repository 131 for which combined health agency case data is sought or queried (e.g., in response to the request for case data identifying FAERS as an electronic data source, outputting combined health agency case data from the central health agency case repository 131 associated with FAERS).

Additionally, the central case data warehouse 130A may include a separate central PV case repository 132 for each medical product or signal product profile (also referred to as a medical product profile). For instance, the central case warehouse 130A may include a first central PV case repository 132 in which trusted case data received form the trusted case repository 146 and associated with Drug X is stored and a second central PV case repository 132 in which trusted case data received from the trusted case repository 146 and associated with Drug Y is stored. In other embodiments, the central case warehouse 130 may include a separate central PV case repository 132 for each separate customer. For instance, the central case warehouse 130A may include a first central PV case repository 132 associated with customer or Pharma X and a second central PV case repository 132 associated with customer or Pharma Y, thereby preventing separate customer data from becoming mistakenly intermingled. In this regard, the central case data warehouse 130A (or the PV repository 132), when requested or queried, may output the trusted case data of the respective central PV case repository 132 for which trusted case data is sought or queried (e.g., in response to the request for case data identifying drug X as a medical product, outputting trusted case data from the central PV case repository 132 associated with drug X).

Moreover, the central case data warehouse 130A may include a separate central additional case repository 133 for each external or additional source of case data. For instance, the central case warehouse 130A may include a first central additional case repository 133 in which social media case data received from a social media case mining repository is stored and a second central additional case repository 133 in which medical literature case data received from a medical literature case repository is stored. In another example, the central case warehouse 130A may include a first central additional case repository 133 in which social media case data received from a first social media case mining repository is stored and a second central additional case repository 133 in which social media case data received from a second social media case mining repository is stored. In this regard, the central case data warehouse 130A (or the additional case repository 133), when requested or queried, may output the additional case data of the respective central additional case repository 133 for which additional case data is sought or queried (e.g., in response to the request for case data identifying the social media mining repository as an electronic data source, outputting additional case data from the central additional case repository 133 associated with the social media mining repository).

FIG. 9B shows a central case data warehouse 130B including a single central health agency case repository 131, a single central PV case repository 132, and a central additional case repository 133. As described herein, the central case data warehouse 130B may include a single central health agency case repository 131 in which all of the health agency case data (after being cleaned and combined) received from the health agency computing systems 112 is stored. In this regard, the combined health agency case data stored therein may still be distinguishable or separable by health agency from which the combined health agency case data was received. For example, a first portion of the combined health agency case data stored within the single central health agency case repository 131 may be distinguishable as associated with or received from the FDA (e.g., FAERS) and a second portion of the combined health agency case data stored within the single central health agency case repository 131 may be distinguishable as associated with or received from the WHO (e.g., Vigibase). In this regard, the central case data warehouse 130A, when requested or queried, may output the portion of the combined health agency case data of the single central health agency case repository 131 for which combined health agency case data is sought or queried (e.g., in response to the request for case data identifying FAERS as an electronic data source, outputting the portion of the combined health agency case data from the central health agency case repository 131 associated with FAERS).

Additionally, the central case data warehouse 130B may include a single central PV case repository 132 in which all of the trusted case data received from the trusted case repository 146 is stored. In this regard, the trusted case data stored therein may still be distinguishable or separable by medical product and/or customer for which the trusted case data is associated. For example, a first portion of the trusted case data stored within the single central PV case repository 132 may be distinguishable as associated with a first customer (e.g., Biopharma 1) and a second portion of the trusted case data stored within the single central PV case repository 132 may be distinguishable as associated with a second customer (e.g., Biopharma 2). In this regard, the central case data warehouse 130A (or the PV repository 132), when requested or queried, may output the portion of the trusted case data of the single central PV case repository 132 for which trusted case data is sought or queried (e.g., in response to the request for case data identifying drug X as a medical product, outputting the portion of the trusted case data from the central PV case repository 132 associated with drug X).

Additionally, the central case data warehouse 130B may include a single central additional case repository 133 in which all of the additional case data received by the provider computing system 104 is stored. In this regard, the additional case data stored therein may still be distinguishable or separable by source from which the additional case data was received. For example, a first portion of the additional case data stored within the single additional case repository 133 may be distinguishable as received from a first social media case repository and a second portion of the additional case data stored within the single additional case repository 133 may be distinguishable as received from a medical literature case repository. In this regard, the central case data warehouse 130A (or the additional case repository 133), when requested or queried, may output the portion of the additional case data of the single central additional case repository 133 for which additional case data is sought or queried (e.g., in response to the request for case data identifying the social media mining repository as an electronic data source, outputting the portion of the additional case data from the central additional case repository 133 associated with the social media mining repository).

FIG. 9C shows the central case data warehouse 130C including a single central case repository 195. The single central case repository 195 may be a repository within which all of the received case data (e.g., the trusted case data from the trusted case repository 146, the combined health agency case data received from the health agency computing systems 112, and the additional case data received from one or more additional repositories) is stored. In this regard, the central case warehouse 130C may combine the different types of case data and store them together within the single central case repository 195 while still maintaining or distinguishing between the types of the case data such that the source of the case data is still identifiable (e.g., each source of case data is included in a separate row or column of a table), and therefore separable.

It should be understood that any of the example embodiments (130A-130C) and the components thereof may be combined and that such combinations are within the scope of this disclosure. For example, the central case data warehouse 130 may include a single central health agency case repository 131 as discussed with regard to FIG. 9A and multiple central PV case repositories 132 as discussed with regard to FIG. 9B, and vice versa. In another example, the central case data warehouse may include a single central health agency case repository 131, multiple central PV case repositories 132, and a single additional case repository 133.

The one or more health agency repositories (also referred to as the central health agency case repository) 131 are each a repository (e.g., a database, cloud storage, etc.) that is structured or configured to receive, store, and manage the cleaned and combined health agency case data received from the health agency computing system 112. For example, the provider computing system 104 may receive health agency case data, clean the health agency case data, combine the health agency case data with medical product data and/or one or more adverse event identifiers, and store the combined health agency case data within the one or more central health agency case repositories 131 of the central case warehouse 130. Each central health agency case repository 131 may be structured according to various database types, such as relational, hierarchical, network, flat, point-in time, and/or object relational. In some embodiments, each central health agency case repository 131 includes a plurality of nonvolatile/non-transitory storage media such as solid-state storage media, hard disk storage media, virtual storage media, cloud-based storage drives, storage servers, and/or the like.

Similarly, the one or more PV repositories (also referred to as central PV case repositories) 132 are each a repository (e.g., a database, cloud storage, etc.) that is structured or configured to receive, store, and manage the trusted case data received from the trusted case repository 146 of the PV circuit 144. Each central PV case repository 132 may be structured according to various database types, such as relational, hierarchical, network, flat, point-in time, and/or object relational. In some embodiments, each central PV case repository 132 includes a plurality of nonvolatile/non-transitory storage media such as solid-state storage media, hard disk storage media, virtual storage media, cloud-based storage drives, storage servers, and/or the like.

Likewise, the central case repository 195 is a repository (e.g., a database, cloud storage, etc.) that is structured or configured to receive, store, and manage central case data generated by the provider computing system 104 (e.g., the processing circuit 122, the central case data warehouse 130, etc.). The central case repository 195 may be structured according to various database types, such as relational, hierarchical, network, flat, point-in time, and/or object relational. In some embodiments, the central case repository 195 includes a plurality of nonvolatile/non-transitory storage media such as solid-state storage media, hard disk storage media, virtual storage media, cloud-based storage drives, storage servers, and/or the like.

The embodiments described herein have been described with reference to the drawings. The drawings illustrate certain details of specific embodiments that implement the systems, methods, and programs described herein. However, describing the embodiments with drawings should not be construed as imposing on the disclosure any limitations that may be present in the drawings.

It should be understood that no claim element herein is to be construed under the provision of 35 U.S.C § 112 (f), unless the element is expressly recited using the phrase "means for."

As used herein, the term "circuit" may include hardware structured to execute the functions described herein. In some embodiments, each respective "circuit" may include machine-readable media for configuring the hardware to execute the functions described herein. The circuit may be embodied as one or more circuitry components including, but not limited to, processing circuitry, network interfaces, peripheral devices, input devices, output devices, sensors, etc. In some embodiments, a circuit may take the form of one or more analog circuits, electronic circuits (e.g., integrated circuits (IC), discrete circuits, system on a chip (SOC) circuits), telecommunication circuits, hybrid circuits, and any other type of "circuit." In this regard, the "circuit" may include any type of component for accomplishing or facilitating achievement of the operations described herein. For example, a circuit as described herein may include one or more transistors, logic gates (e.g., NAND, AND, NOR, OR, XOR, NOT, XNOR), resistors, multiplexors, registers, capacitors, inductors, diodes, wiring, and so on.

The "circuit" may also include one or more processors communicably coupled to one or more memory or memory devices. In this regard, the one or more processors may execute instructions stored in the memory or may execute instructions otherwise accessible to the one or more processors. In some embodiments, the one or more processors may be embodied in various ways. The one or more processors may be constructed in a manner sufficient to perform at least the operations described herein. In some embodiments, the one or more processors may be shared by multiple circuits (e.g., circuit A and circuit B may comprise or otherwise share the same processor which, in some example embodiments, may execute instructions stored, or otherwise accessed, via different areas of memory). Alternatively or additionally, the one or more processors may be structured to perform or otherwise execute certain operations independent of one or more co-processors. In other embodiments, two or more processors may be coupled via a bus to enable independent, parallel, pipelined, or multi-threaded instruction execution. Each processor may be implemented as one or more general purpose processors, application specific integrated circuits (ASICs), field programmable gate arrays (FPGAs), digital signal processors (DSPs), or other suitable electronic data processing components structured to execute instructions provided by the memory. The one or more processors may take the form of a single core processor, a multi-core processor (e.g., dual core, quad core, etc.), microprocessor, etc. In some embodiments, the one or more processors may be external to the apparatus. For example, the one or more processors may be a remote processor (e.g., a cloud-based processor). Alternatively or additionally, the one or more processors may be internal and/or local to the apparatus. In this regard, a circuit or components thereof may be disposed locally (e.g., as part of a local server, a local computing system) or remotely (e.g., as part of a remote server such as a cloud-based server). To that end, a "circuit" as described herein may include components that are distributed across one or more locations. Further, the circuits of the processing circuit described herein may be distributed across one or more locations (e.g., each as part of one or more remote servers).

An example system for implementing the overall system or portions of the embodiments might include a general purpose computing device in the form of computers, including a processing unit, a system memory, and a system bus that couples various system components including the system memory to the processing unit. Each memory device may include non-transient volatile storage media, non-volatile storage media, non-transitory storage media (e.g., one or more volatile and/or non-volatile memories), etc. In some embodiments, the non-volatile storage media may take the form of ROM, flash memory (e.g., flash memory such as NAND, 3D NAND, NOR, 3D NOR), EEPROM, MRAM, magnetic storage, hard disks, optical disks, etc. Combinations of the above are also included within the scope of machine-readable media. In this regard, machine-executable instructions comprise, for example, instructions and data which cause a general purpose computer, special purpose computer, or special purpose processing machine to perform a certain function or group of functions. Each respective memory device may be operable to maintain or otherwise store data relating to the operations performed by one or more associated circuits, including processor instructions and related data (e.g., database components, object code components, script components), in accordance with the example embodiments described herein.

It should also be noted that the term "input devices," as described herein, may include any type of input device including, but not limited to, a keyboard, a keypad, a mouse, a joystick, or other input devices performing a similar function. Comparatively, the term "output device," as described herein, may include any type of output device including, but not limited to, a computer monitor, printer, facsimile machine, or other output devices performing a similar function.

It should be noted that the term "field," as described herein may include any form of an input field through which the user interfaces shown and described may receive input from a user of a computing device. For instance, the term "field" may include a text field, a drop-down box and selectable options, a lookup box, a search bar, an icon, one or more checkboxes, one or more radio buttons, a button, a toggle, a date field, a slider, and the like. Further, each "field" may include and/or receive data that is associated with a data object as described herein.

It should be noted that although the diagrams herein may show a specific order and composition of method steps, it is understood that the order of these steps may differ from what is depicted. For example, two or more steps may be performed concurrently or with partial concurrence. Also, some method steps that are performed as discrete steps may be combined, steps being performed as a combined step may be separated into discrete steps, the sequence of certain processes may be reversed or otherwise varied. The order or sequence of any element or apparatus may be varied or substituted according to alternative embodiments. Accordingly, all such modifications are intended to be included within the scope of the present disclosure as defined in the appended claims. Such variations will depend on the machine-readable media and hardware systems chosen and on designer choice. It is understood that all such variations are within the scope of the disclosure. Likewise, software and web implementations of the present disclosure could be accomplished with standard programming techniques with rule-based logic and other logic to accomplish the various database searching steps, correlation steps, comparison steps, and decision steps.

The foregoing description of embodiments has been presented for purposes of illustration and description. It is not intended to be exhaustive or to limit the disclosure to the precise form disclosed, and modifications and variations are possible in light of the above teachings or may be acquired from this disclosure. The embodiments were chosen and described in order to explain the principles of the disclosure and its practical application to enable one skilled in the art to utilize the various embodiments and with various modifications as are suited to the particular use contemplated. Other substitutions, modifications, changes, and omissions may be made in the design, operating conditions and embodiment of the embodiments without departing from the scope of the present disclosure as expressed in the appended claim.

What is claimed is:

1. A method for determining a potential signal in a central case data storage system, wherein the central case data storage system comprises a provider computing system communicably coupled to a secure network, wherein the provider computing system comprises a central case data warehouse for storing case data, the method comprising:

receiving, by a network interface of the provider computing system, a request for first case data from a user computing device via the secure network, wherein the request identifies a timeframe and a medical product;

receiving, by the network interface, a statistical value minimum from the user computing device via the secure network;

selecting, by a processing circuit of the provider computing system, the first case data from the central case data warehouse based on the request;

determining, by the processing circuit, a first statistical value based on the first case data, wherein the first statistical value is at least one of: a case count, a proportional reporting ratio (PRR) value, a chi-squared value, an Empirical Bayes (EB) value, or an Interaction Signal Score (INTSS) value;

determining, by the processing circuit, one or more signals based on the first statistical value and the statistical value minimum, wherein each signal of the one or more signals represents an adverse event related to the medical product;

transmitting, by the network interface, the first statistical value, the first case data, and the one or more signals via the secure network to the user computing device to be displayed on a first webpage including:

an interactive statistical value chart or graph, an interactive heat map of the adverse event of the one or more signals, and an interactive list of the one or more signals and one or more corresponding track signal buttons;

receiving, by the network interface and in response to a selection of one of the one or more track signal buttons, a request to track a potential signal from the user computing device;

receiving, by the central case data warehouse, new case data associated with the potential signal from at least one of a health agency computing system or a trusted case repository;

selecting, by the processing circuit, the new case data associated with the potential signal from the central case data warehouse;

determining, by the processing circuit, a change to the potential signal based on the new case data;

generating, by the processing circuit and in response to determining the change to the potential signal, one or more alerts; and transmitting, by the network interface and via the secure network, the one or more alerts to the user computing device to be displayed on a second webpage including:

a state section, a signal details section, a signal sources section identifying a first electronic data source associated with the health agency computing system and a second electronic data source associated with trusted case repository, a case listing section, and a workbench button.

2. The method of claim 1, wherein timeframe includes a start date and end date, wherein the first case data includes a date, and wherein selecting the first case data from the central case data warehouse based on the request comprises:

determining, by the processing circuit, the date of the first case data is between the start date and the end date of the timeframe; and selecting, by the processing circuit and in response to determining the date of the first case data is between the start date and the end date of the timeframe, the first case data from the central case data warehouse.

3. The method of claim 1, wherein the request identifies a first medical product identifier of the medical product, wherein the first case data includes a second medical product identifier, and wherein selecting the first case data from the central case data warehouse based on the request comprises:

determining, by the processing circuit, the first medical product identifier of the first case data matches the second medical product identifier of the request; and selecting, by the processing circuit and in response to determining the first medical product identifier of the first case data matches the second medical product identifier, the first case data from the central case data warehouse.

4. The method of claim 1, wherein the request includes a filter that is at least one of an age group, a gender, or a seriousness, and wherein the method further comprises:

filtering, by the processing circuit, the first case data based on the filter of the request, wherein the first statistical value is determined based on the filtered first case data.

5. The method of claim 1, wherein the central case data warehouse comprises a central health agency case repository and one or more central PV repositories.

6. The method of claim 1, wherein determining the one or more signals based on the first statistical value and the statistical value minimum comprises:

determining, by the processing circuit, the first statistical value is greater than the statistical value minimum; and determining, by the processing circuit and in response to determining the first statistical value is greater than the statistical value minimum, the one or more signals.

7. A method for determining a potential signal in a central case data storage system, wherein the central case data storage system comprises a provider computing system communicably coupled to a secure network, wherein the provider computing system comprises a central case data warehouse for storing case data, the method comprising:

receiving, by a network interface of the provider computing system, a request for first case data from a user computing device via the secure network, wherein the request identifies a timeframe and a medical product;

receiving, by the network interface, a statistical value minimum from the user computing device via the secure network;

selecting, by a processing circuit of the provider computing system, the first case data from the central case data warehouse based on the request;

determining, by the processing circuit, a first statistical value based on the first case data, wherein the first statistical value is at least one: an Empirical Bayes Geometric Mean (EBGM) value, an EB05 value, or an EB95 value;

determining, by the processing circuit, one or more signals based on the first statistical value and the statistical value minimum, wherein each signal of the one or more signals represents an adverse event related to the medical product;

transmitting, by the network interface, the first statistical value, the first case data, and the one or more signals via the secure network to the user computing device to be displayed on a first webpage including:

an interactive statistical value chart or graph, an interactive heat map of the adverse event of the one or more signals, and an interactive list of the one or more signals and one or more corresponding track signal buttons;

receiving, by the network interface and in response to a selection of one of the one or more track signal buttons, a request to track a potential signal from the user computing device;

receiving, by the central case data warehouse, new case data associated with the potential signal from at least one of a health agency computing system or a trusted case repository;

selecting, by the processing circuit, the new case data associated with the potential signal from the central case data warehouse;

determining, by the processing circuit, a change to the potential signal based on the new case data;

generating, by the processing circuit and in response to determining the change to the potential signal, one or more alerts;

transmitting, by the network interface and via the secure network, the one or more alerts to the user computing device to be displayed on a second webpage including:

a state section, a signal details section, a signal sources section including identifying a first electronic data source associated with the health agency computing system and a second electronic data source associated with trusted case repository, a case listing section, and a workbench button.

8. The method of claim 7, wherein the timeframe includes a start date and end date, wherein the first case data includes a date, and wherein selecting the first case data from the central case data warehouse based on the request comprises:

determining, by the processing circuit, the date of the first case data is between the start date and the end date of the timeframe; and selecting, by the processing circuit and in response to determining the date of the first case data is between the start date and the end date of the timeframe, the first case data from the central case data warehouse.

9. The method of claim 7, wherein the request includes a filter that is at least one of an age group, a gender, or a seriousness, and wherein the method further comprises:

filtering, by the processing circuit, the first case data based on the filter of the request, wherein the first statistical value is determined based on the filtered first case data.

10. The method of claim 7, wherein the request identifies a first medical product identifier of the medical product, wherein the first case data includes a second medical product identifier, and wherein selecting the first case data from the central case data warehouse based on the request comprises:

determining, by the processing circuit, the first medical product identifier of the first case data matches the second medical product identifier of the request; and selecting, by the processing circuit and in response to determining the first medical product identifier of the first case data matches the second medical product identifier of the request, the first case data from the central case data warehouse.

11. The method of claim 7, wherein the central case data warehouse comprises a central health agency case repository and one or more central PV repositories.

12. The method of claim 7, wherein determining the one or more signals based on the first statistical value and the statistical value minimum comprises:

determining, by the processing circuit, the first statistical value is greater than the statistical value minimum; and determining, by the processing circuit and in response to determining the first statistical value is greater than the statistical value minimum, the one or more signals.

* * * * *